US012735745B2

(12) United States Patent
Kwiatkowski, Jr. et al.

(10) Patent No.: US 12,735,745 B2
(45) **Date of Patent: *Sep. 15, 2026**

(54) FUS/TLS-BASED COMPOUNDS AND METHODS FOR DIAGNOSIS, TREATMENT AND PREVENTION OF AMYOTROPHIC LATERAL SCLEROSIS AND RELATED MOTOR NEURON DISEASES

(71) Applicant: The General Hospital Corporation, Boston, MA (US)

(72) Inventors: Thomas J. Kwiatkowski, Jr., Cambridge, MA (US); Robert H. Brown, Jr., Needham, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/325,279

(22) Filed: May 20, 2021

(65) Prior Publication Data

US 2021/0388444 A1 Dec. 16, 2021

Related U.S. Application Data

(60) Division of application No. 14/834,737, filed on Aug. 25, 2015, now Pat. No. 11,041,204, which is a continuation of application No. 13/055,482, filed as application No. PCT/US2009/004205 on Jul. 21, 2009, now Pat. No. 9,150,860.

(60) Provisional application No. 61/135,689, filed on Jul. 22, 2008.

(51) Int. Cl.

| | |
|---|---|
| ***C12Q 1/6883*** | (2018.01) |
| ***C12N 15/113*** | (2010.01) |
| ***C12Q 1/6837*** | (2018.01) |
| ***G01N 33/68*** | (2006.01) |

(52) U.S. Cl.

CPC ........ *C12Q 1/6883* (2013.01); *C12N 15/1135* (2013.01); *C12Q 1/6837* (2013.01); *G01N 33/6896* (2013.01); *C12N 2310/14* (2013.01); *C12Q 2600/136* (2013.01); *C12Q 2600/156* (2013.01); *C12Q 2600/158* (2013.01); *C12Q 2600/172* (2013.01); *G01N 2800/28* (2013.01)

(58) Field of Classification Search

CPC ................ C12Q 1/6837; C12Q 1/6883; C12Q 2600/156; C12Q 2600/136; C12Q 2600/172; C12Q 2600/158

See application file for complete search history.

(56) References Cited

U.S. PATENT DOCUMENTS

| | | | | |
|---|---|---|---|---|
| 5,843,641 | A | 12/1998 | Brown et al. | |
| 6,723,893 | B1 | 4/2004 | Brown et al. | |
| 9,150,860 | B2 | 10/2015 | Kwiatkowski, Jr. et al. | |
| 11,041,204 | B2 | 6/2021 | Kwiatkowski, Jr. et al. | |
| 2001/0053519 | A1 | 12/2001 | Fodor et al. | |
| 2004/0137450 | A1 | 7/2004 | Shinji et al. | |
| 2004/0208792 | A1* | 10/2004 | Linton | C12Q 1/6858 435/286.1 |
| 2007/0009899 | A1* | 1/2007 | Mounts | C12Q 1/6883 435/6.16 |
| 2007/0202537 | A1 | 8/2007 | Lingappa et al. | |

FOREIGN PATENT DOCUMENTS

| | | | |
|---|---|---|---|
| WO | WO 2004/108899 | A2 | 12/2004 |
| WO | WO 2006/034573 | * | 4/2006 |
| WO | WO 2008/085984 | A1 | 7/2008 |

OTHER PUBLICATIONS

P Carninci, et al. "The transcriptional landscape of the mammalian genome" Science . Sep. 2, 2005;309(5740):1559-63 and the Supporting on Line Material. (Year: 2005).*

GenBank Locus: BB620535 "BB620535 RIKEN full-length enriched mouse cDNA library, C57BL/6J forelimb 13 days embryo Mus musculus cDNA clone 5930431H10 5', mRNA sequence", Nov. 8, 2005. printed from https://www.ncbi.nlm.nih.gov (Year: 2005).*

GenBank Locus: HG994409 "Canis lupus genome assembly, chromosome: 26" Mar. 24, 2021. printed from https://www.ncbi.nlm.nih.gov (Year: 2021).*

GenBank Locus: OV277462 "Meles meles genome assembly, chromosome: 21" Mar. 21, 2022. printed from https://www.ncbi.nlm.nih.gov (Year: 2022).*

Kwiatkowski (Science vol. 323 Feb. 27, 2009 pp. 1205-1208).*

Hui (Current Protocols in Human Genetics 2.10.1-2.10.8 Jan. 2008).*

GenBank (Accession NM_004960 Version NM_004960.2 Jan. 26, 2005).*

Ahern (The Scientist, vol. 9 #Jul. 15, 24, 1995).*

NEB catalog (1998/1999 pp. 121, 284).*

Rothstein (PNAS 1994 vol. 91 pp. 4155-4159).*

Vance (Science vol. 323 Feb. 27, 2009 pp. 1208-1211).*

[No Author Listed] (Japanese) Societas Neurologica, ALS Treatment Guideline, Published by Societas Neurologica Japonica in 2002.

[No Author Listed] NIH—Motor Neuron Diseases Fact Sheet. Retrieved from www.ninds.nih.gov on Sep. 23, 2013. 5 pages.

(Continued)

*Primary Examiner* — Amanda Haney

(74) *Attorney, Agent, or Firm* — Wolf, Greenfield & Sacks, P.C.

(57) ABSTRACT

The invention provides novel FUS/TLS nucleic acids and proteins that comprise one or more genetic markers (for example, single nucleotide polymorphisms) and methods of use thereof including methods relating to the diagnosis of ALS or other related motor neuron disease by virtue of the presence of the mutant FUS/TLS sequence(s).

4 Claims, 7 Drawing Sheets

Specification includes a Sequence Listing.

(56) References Cited

OTHER PUBLICATIONS

Battistini et al., SODI mutations in amyotrophic lateral sclerosis. Results from a multicenter Italian study. I Neural. Jul. 2005;252(7):782-8. Epub Mar. 29, 2005.
Caldwell et al., Full-length cDNAs from chicken bursal lymphocytes to facilitate gene function analysis. Genome Biol. 2005;6(1):R6. doi: 10.1186/GB-2004-6-1-r6. Epub Dec. 23, 2004.
Chio et al., Two Italian kindreds with familial amyotrophic lateral sclerosis due to FUS mutation. Neurobiol Aging. Aug. 2009;30(8):1272-5. Epub May 17, 2009.
Doi et al., RNA-binding protein TLS is a major nuclear aggregate-interacting protein in huntingtin exon 1 with expanded polyglutamine-expressing cells. J. Biol Chem. Mar. 7, 2008;283(10):6489-500. doi:10.1074/jbc.M705306200. Epub Dec. 31, 2007.
Gellera et al., Identification of new ANG gene mutations in a large cohort of Italian patients with amyotrophic lateral sclerosis. Neurogenetics. Feb. 2008;9(1):33-40. Epub Dec. 18, 2007.
Genbank Submission; NIH/NCBI, Accession No. AF071213. Morohoshi et al., Sep. 12, 1998. 7 pages.
Genbank Submission; NIH/NCBI, Accession No. AJ731114. Caldwell et al., 2004. 1 page.
Genbank Submission; NIH/NCBI, Accession No. AW009325.1, Sep. 9, 1999. 2 pages.
Genbank Submission; NIH/NCBI, Accession No. NM_004960.2. Kaplowitz et al., Jun. 27, 2007. 5 pages.
Hegele R, SNP judgments and freedom of association. Arterioscler Thromb Vasc Biol. Jul. 1, 2002;22(7):1058-61.
Juppner H., Functional properties of the PTH/PTHrP receptor. Bone. Aug. 1995;17(2 Suppl):39S-42S.
Kurg et al., Arrayed primer extension: solid-phase four-color DNA resequencing and mutation detection technology. Genet Test. 2000;4(1):1-7. doi: 10.1089/109065700316408.
Kwiatkowski et al., Mutations in the FUS/TLS gene on chromosome 16 cause familial amyotrophic lateral sclerosis. Science. Feb. 27, 2009;323(5918): 1205-8.
Morohoshi et al., Genomic structure of the human RBP56/hTAFII68 and FUS/TLS genes. Gene. Oct. 23, 1998;221(2):191-8.
Rabbitts et al., Fusion of the dominant negative transcription regulator CHOP with a novel gene FUS by translocation t(12;16) in malignant liposarcoma. Nat Genet. Jun. 1993;4(2):175-80. doi: 10.1038/ng0693-175.
Vance et al., Mutations in FUS, an RNA processing protein, cause familial amyotrophic lateral sclerosis type 6. Science. Feb. 27, 2009;323(5918):1208-1211.
Zhu et al., Directly labeled DNA probes using fluorescent nucleotides with different length linkers. Nucleic Acids Res. Aug. 25, 1994;22(16):3418-22. doi: 10.1093/nar/22.16.3418.

* cited by examiner

| | 480 | 481 | 491 | 501 | 511 | 521 526 |
|---|---|---|---|---|---|---|
| **ALS** | | | | | | **CG** |
| **ALS** | | | | | **(SC)Q** | **HLG SR** |
| Human | Y | DRGGYRGRGGD | RGGFRGGRGG | GDRGGFGPGK | MDSRGEHRQD | RRERPY |
| Chimp | Y | DRGGYRGRGGD | RGGFRGGRGG | GDRGGFGPGK | MDSRGEHRQD | RRERPY |
| Macaque | Y | DRGGYRGRGGD | RGGFRGGRGG | GDRGGFGPGK | MDSRGEHRQD | RRERP- |
| Squirrel | Y | DRGGYRGRGGD | RGGFRGGRGG | GDRGGFGPGK | MDS------- | ----- |
| Pig | - | ----------- | ---------- | ---------- | ---------- | ------ |
| Elephant | Y | DRGGYRGRGGD | RGGFRGGRGG | GDRGGFGPGK | MDSRGEHRQD | RRERP- |
| Cow | Y | DRGGYRGRGGD | RGGFRGGRGG | GDRGGFGPGK | MDSRGEHRQD | RRERPY |
| Mouse | Y | DRGGYRGRGGD | RGGFRGGRGG | GDRGGFGPGK | MDSRGEHRQD | RRERPY |
| Rat | Y | DRGGYRGRGGD | RGGFRGGRGG | GDRGGFGPGK | MDSRGEHRQD | RRERPY |
| Hedgehog 1 | Y | DRGGYRGRGGD | RGGFRGGRGG | GDRGGFGPGK | MDSRGEHRQD | RRERPY |
| Rock rabbit | Y | DRGGYRGRGGD | RGGFRGGRGG | GDRGGFGPGK | MDSRGEHRQD | RRERP- |
| Hedgehog 2 | Y | D-GGYRGRGGD | RGGFQGGWGG | GDRGGFGPGK | MDSRGDHRQD | HRERPY |
| Brown bat | Y | DQGGYGGHDGD | RGGFRG-RGA | GDRGGFVPGK | MDS-GDHRQD | RRERPY |
| Armadillo | C | DWGSYGGRDCG | FGG-----DG | GDRGGSGHGK | VDSRGGHRQD | RWERP- |
| Oppossum | Y | DRGGYRGRGGD | RGGFRGGRGG | GDRGGFGPGK | MDSRGEHRQD | RRERPY |
| Dog | Y | DRGGYRGRGGD | RGGFRGGRGG | GDRGGFGPGK | MDSRGEHRQD | RRERPY |
| Xenopus | F | DRGGFRGRGGD | RGGFRG GRG | GDRGGFGPGK | MDSRGDHRQD | RRDRPY |
| Zebrafish | F | DRGGFRGRGGD | RGGFRGG RG | GDRGGFGPGK | MDSRGDHRHD | RRDRPY |
| Puffer fish | F | DRGGFRGRGGD | RGGFRGG RG | GERGGYGPGK | MDARGDRRQE | RRGRPY |

Fig. 1C

FUS/TLS-BASED COMPOUNDS AND METHODS FOR DIAGNOSIS, TREATMENT AND PREVENTION OF AMYOTROPHIC LATERAL SCLEROSIS AND RELATED MOTOR NEURON DISEASES

RELATED APPLICATIONS

This application is a divisional of U.S. application Ser. No. 14/834,737, filed Aug. 25, 2015, which is a continuation of U.S. application Ser. No. 13/055,482, filed Jan. 24, 2011, which is a national stage filing under 35 U.S.C. § 371 of international application PCT/US2009/004205, filed Jul. 21, 2009, which was published under PCT Article 21(2) in English, and claims the benefit under 35 U.S.C. 119(e) of U.S. provisional application Ser. No. 61/135,689, filed Jul. 22, 2008, the entire contents of which is incorporated by reference herein.

GOVERNMENT FUNDING

This invention was made with Government support from the National Institute of Neurological Disorders and Stroke (NINDS) under Grant No. R01 NS050557-01. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 18, 2021, is named M076570101US03-SEQ-JRV.txt, and is 31,227 bytes in size.

FIELD OF THE INVENTION

The invention relates to diagnosis and treatment of motor neuron diseases, particularly amyotrophic lateral sclerosis.

BACKGROUND OF THE INVENTION

Amyotrophic lateral sclerosis (ALS) is a progressive, fatal neurodegenerative disorder. Its incidence has been reported to be 0.6-2.6/100,000 (Roman, J Neurol Neurosurg Psychiatry. 1996. 61(2): 131-7) with a slight male predominance. The disease incidence peaks in the sixth decade of life (Nelson, Clin. Neurosci. 3, 327 (1995)); survival is typically 2 to 5 years. ALS inevitably leads to death from respiratory paralysis in the absence of mechanical ventilation. Familial cases account for about 10% of ALS; mutations in cytosolic copper-zinc superoxide dismutase 1 (SOD1) have been shown to account for 20-25% of these familial cases (Rosen, Nature 364, 362 (1993)). Mutations in vesicle-associated membrane protein-associated protein (VAPB) have been shown to cause either classical ALS or atypical motor neuron disease in a small number of Brazilian families. A handful of other genes have been implicated in atypical motor neuron disease, including upper-motor-neuron-predominant ALS2 (alsin), juvenile ALS (senataxin), and lower motor neuropathy (DCTN1). A second form of juvenile inherited ALS (recessive in this case) has been linked to chromosome 15q (Hentati et al., Neurogenetics 2, 55 (1998)). In the majority of familial classical ALS cases, however, the causative gene is unknown. High-penetrance classical ALS pedigrees have been reported with linkage to chromosomes 16, and 18, while families with ALS with and without frontotemporal dementia have been reported with linkage to chromosome 9.

SUMMARY OF THE INVENTION

We have discovered that mutations in the human FUS/TLS gene are associated with human amyotrophic lateral sclerosis (ALS) and related motor neuron diseases. Here we report mutations in the FUS/TLS gene on chromosome 16 associated with both dominant classical and apparently recessive, atypical, ALS. Accordingly the invention provides methods for the diagnosis and treatment of amyotrophic lateral sclerosis and other motor neuron diseases. Methods are provided for treating familial amyotrophic lateral sclerosis and amyotrophic lateral sclerosis as well as other motor neuron diseases which are the result of altered FUS/TLS activity and/or altered FUS/TLS physical characteristics. In addition, therapeutics for diseases caused by alterations in the FUS/TLS biochemical pathway are provided.

In one aspect, the invention provides a method for diagnosing ALS or related motor neuron disease in a subject comprising detecting in a sample obtained from an individual one or more genetic markers in a FUS/TLS nucleic acid or fragment thereof, wherein the one or more genetic markers are selected from the group consisting of C1551G, C1561G, G1542T, G1543T, C1561T, G1562A, A1564G or G1572C, and wherein the presence of the one or more markers indicates that the individual has ALS or a related motor neuron disease or has a genetic predisposition or susceptibility for ALS or a related motor neuron disease.

In one embodiment, the mutation(s) is/are in exon 15 of FUS/TLS. In one embodiment, one or more of the genetic markers encodes an amino acid change in the FUS/TLS protein (relative to wild type). In one embodiment, the amino acid change is at H517Q, R521G, R514S, G515C, R521C, R521H, R522G, or R524S. In one embodiment, the method comprises detecting a haplotype comprising all 8 markers. In one embodiment, the nucleic acid is DNA, genomic DNA, RNA, cDNA, hnRNA or mRNA. In one embodiment, the detection is accomplished by sequencing, hybridization, restriction fragment analysis, oligonucleotide ligation assay or allele specific PCR. In one embodiment, the one or more genetic markers are identified using an antibody or antigen-binding fragment thereof that binds selectively to the mutant FUS/TLS protein.

In another aspect, the invention provides a diagnostic kit and/or a research kit, comprising at least one combination of probes for detecting at least one of the genetic markers described herein.

In another aspect, the invention provides a method of treatment or prophylaxis of ALS or related motor neuron disease comprising performing the diagnostic method as described above or otherwise herein to identify an individual that has ALS or related motor neuron disease or has a genetic predisposition or susceptibility for ALS or related motor neuron disease, and administering to the individual a therapeutically effective amount of a composition suitable to delay, reduce or prevent ALS or the related motor neuron disease in the individual and/or treating the individual with therapy.

In one embodiment, the composition comprises a modulator of mutant FUS/TLS activity. In another embodiment, the modulator is a siRNA molecule that reduces mutant FUS/TLS expression. In another embodiment, the modulator is an expression vector that increases wild-type FUS/TLS expression.

In another aspect, the invention provides a genetically engineered organism comprising one or more genetic markers selected from the group consisting of C1551G, C1561G, G1542T, G1543T, C1561T, G1562A, A1564G or G1572C in a FUS/TLS gene or one or more genetic markers selected from the group consisting of H517Q, R521G, R514S, G515C, R521C, R521H, R522G, or R524S in a FUS/TLS protein.

In one embodiment, the genetic marker is/are in exon 15 of FUS/TLS. In another embodiment, the organism is a mouse.

In still another aspect, the invention provides a method for screening for molecules that bind selectively to a mutant FUS/TLS protein or nucleic acid comprising contacting wild-type and mutant FUS/TLS nucleic acid or protein with a candidate molecule, and measuring binding of the candidate molecule to wild-type and mutant FUS/TLS nucleic acid or protein, wherein a level of binding to mutant FUS/TLS that is 5-fold greater than the level of binding to wild-type FUS/TLS is indicative of a molecule that binds selectively to mutant FUS/TLS.

The invention further features methods of diagnosing an increased likelihood of developing cell death disease in a patient. The methods include analyzing the DNA of the patient to determine whether the DNA contains a mutation in the FUS/TLS coding sequence, such a mutation being an indication that the patient has an increased likelihood of developing a cell death disease. The methods may be used to diagnose a cell death disease, particularly neurodegenerative disease, more particularly amyotrophic lateral sclerosis (ALS).

ALS may be familial, sporadic typical, or atypical in nature.

The methods described herein may also be used to determine the likelihood of developing another neurodegenerative condition such as but not limited to Parkinson's disease, Huntington's disease, Alzheimer's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome, and Hallervorden-Spatz disease.

The methods may include amplifying a FUS/TLS-encoding gene of the patient, and then analyzing the amplified gene. The DNA may be analyzed by nucleotide sequencing, SSCP analysis, RFMP, heteroduplex analysis or RFLP analysis. The amplifying may be carried out by PCR reaction, by reverse transcriptase PCR or by any other method available to obtain a sufficient amount of DNA.

Antibodies which recognize (and thus bind) proteins or peptides coded by the mutant nucleic acids of the invention but which do not recognize (and thus do not bind) proteins or peptides coded by the wild-type (non-SNP mutation containing nucleic acids) may be used for the diagnosis of amyotrophic lateral sclerosis, including familial ALS.

According to another aspect of the invention, diagnostic kits and/or research kits are provided. The kits include at least one combination of probes for detecting at least one of the mutations described herein.

The invention further provides kits for the diagnosis of a cell death disease, such as ALS, in a subject. The kits may include one or more FUS/TLS gene-specific PCR primers or antibodies recognizing the FUS/TLS mutant proteins or peptides. The PCR primers may include a FUS-specific nucleic acid sequence, a TLS-specific nucleic acid sequence, and/or a FUS/TLS-specific nucleic acid sequence, whether normal or mutant (as for example provided by the invention as a result of SNP mutations in the FUS/TLS sequence. These kits may be used to diagnose any of the above-referenced diseases.

The invention provides methods for performing a diagnostic method as described herein to identify an individual that has a genetic predisposition or susceptibility for ALS or other related motor neuron disease, and administering to the individual a therapeutically effective amount of a composition suitable to delay, reduce or prevent ALS or the other related motor neuron disease in the individual and/or treating the individual with therapy.

The invention further provides a method for treating a patient with a disease involving a mutant FUS/TLS gene. This method includes first identifying a mutant FUS/TLS gene in the DNA of the patient, and second administering to the patient a therapeutic amount of the anti-sense RNA homolog of a gene encoding a FUS/TLS mutant protein.

Also included is a method for treating a patient with a disease involving a mutant FUS/TLS gene, wherein the mutant FUS/TLS gene in the DNA is identified in the patient, and a therapeutic amount of a transgene encoding the wild-type FUS/TLS homolog is administered.

Also part of the invention is a method of treating a patient with a disease involving a FUS/TLS gene by administering to the patient an antibody which is sufficient to partially inactivate the mutant FUS/TLS protein.

The diagnostic methods of the invention also can be used to determine when not to treat an individual suspected of having ALS or other related motor neuron disease as a result of the screening results.

The invention further provides the SNP containing FUS/TLS nucleic acids of the invention, protein or peptides encoded by such nucleic acids, binding partners that bind specifically to the nucleic acids or proteins, vectors and cells (e.g., bacterial or mammalian) containing such nucleic acids, and methods of use thereof.

These and other aspects of the invention, as well as various embodiments thereof, will become more apparent in reference to the drawings and detailed description of the invention.

BRIEF DESCRIPTION OF THE DRAWINGS

FIGS. 1A-1C. FIGS. 1A and 1B: FUS/TLS ALS index pedigrees and gene information. FIG. 1C: Evolutionary conservation of FUS/TLS. Mutations observed in ALS patients are shown, in red, above the human sequence. "(SC)" refers to a 2 bp mutation (in cis) in one individual causing 2 consecutive mis-sense mutations (R514S and G515C). In FIG. 1C, "Human" corresponds to SEQ ID NO:5; "Chimp" corresponds to SEQ ID NO:6; "Macaque" corresponds to SEQ ID NO:7; "Squirrel" corresponds to SEQ ID NO:8; "Elephant" corresponds to SEQ ID NO:9; "Cow" corresponds to SEQ ID NO: 10; "Mouse" corresponds to SEQ ID NO: 11; "Rat" corresponds to SEQ ID NO:12; "Hedgehog 1" corresponds to SEQ ID NO: 13; "Rock rabbit" corresponds to SEQ ID NO: 14; "Hedgehog 2" corresponds to SEQ ID NO: 15; "Brown bat" corresponds to SEQ ID NO:16; "Armadillo" corresponds to SEQ ID NO: 17; "Oppossum" corresponds to SEQ ID NO: 18; "Dog" corresponds to SEQ ID NO: 19; "*Xenopus*" corresponds to SEQ ID NO:20; "Zebrafish" corresponds to SEQ ID NO:21; and "Puffer fish" corresponds to SEQ ID NO:22.

FIG. 2A: F55 ALS patient vs. control, brain (cortex) stained with anti-NeuN/gfp and anti-lipofuschin/Cy3 antibodies, merged images (left) or with anti-FUS/TLS antibody+DAB secondary. FIG. 2B: F55 ALS patient vs. control, spinal cord stained with anti-NeuN/Cy3 and anti-FUS/TLS antibodies and DAPI, with merged images.

FIG. 3A: SK-NAS (top) or N2A (bottom) cells transfected with wild-type or mutant (F55=R521G or F577=H517Q) recombinant FUS/TLS-gfp fusion protein, counterstained with DAPI, merged images. Percentage of cells observed with significant nuclear vs. cytosolic FUS/TLS staining indicated to right. FIG. 3B: Cell fractionation studies. SK-NAS cells transfected with wild-type or mutant (F55=R521G or F577=H517Q) recombinant FUS/TLS-gfp fusion protein, harvested and fractionated at 24 hrs., Western blotted and stained with anti-gfp antibody/ECL. Lamin and GAPDH loading control staining below, densitometric ratios to right.

DETAILED DESCRIPTION OF THE INVENTION

Figure 1A:
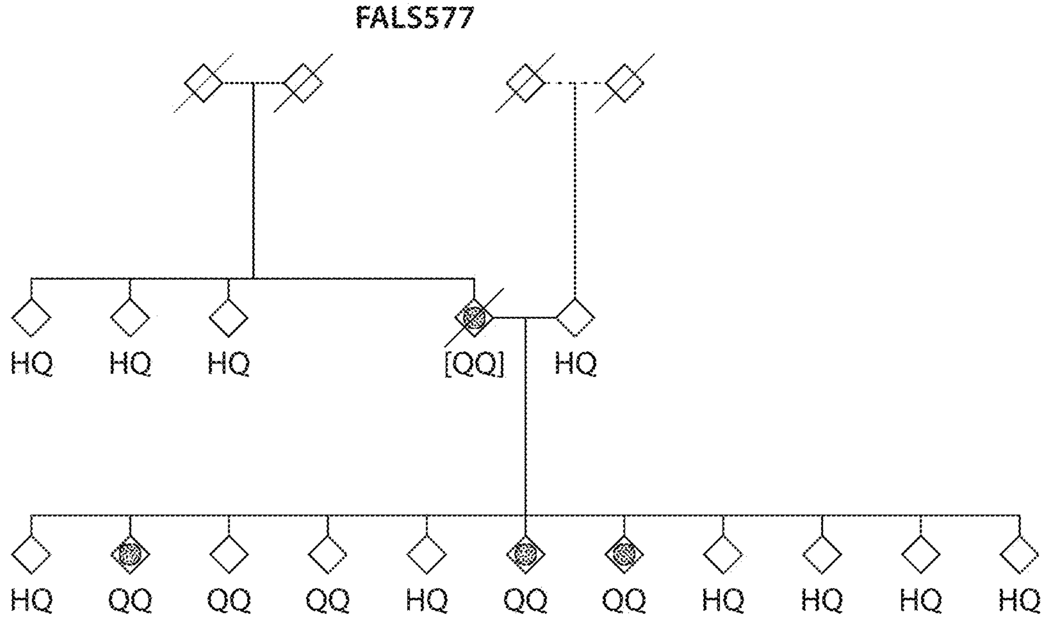

We have identified mutations in the FUS/TLS gene in human ALS patients (including dominantly- and recessively-inherited familial ALS). Using the knowledge of the mutations in this gene sequence, and clinical information on patients carrying FUS/TLS mutations, ALS can be diagnosed and predicted in symptomatic and at-risk individuals. Moreover, mutations can be introduced into the FUS/TLS gene in experimental animals and cultured cells to study ALS and motor neuron biology. Such animals and cells can be used to develop and test therapeutic interventions (including drugs, siRNA, and gene and protein therapy) for use in human patients with ALS and related disorders.

The official full name of the FUS gene is "fusion (involved in t(12;16) in malignant liposarcoma)". The gene is also known as FUS, TLS; FUS/TLS; CHOP; FUS1; FUS-CHOP; TLS/CHOP; and hnRNP-P2. The gene has 15 exons and a transcript length of 2,002 nucleotides. The FUS/TLS gene encodes a 75 kDa DNA-pairing nuclear protein that binds both single-stranded and double-stranded DNA and promotes ATP-independent annealing of complementary single-stranded DNAs and D-loop formation in superhelical double-stranded DNA. The length of the protein is 526 amino acid residues. FUS/TLS sequences are provided herein as follows and are contained in the Sequence Listing attached herewith and incorporated herein:

SEQ ID NO:1 is the gene sequence;

SEQ ID NO:2 is the cDNA sequence;

SEQ ID NO:3 is the protein coding sequence; and

SEQ ID NO:4 is the amino acid sequence of the protein.

FUS/TLS has been found to be a major nuclear-aggregate-interacting protein in a model of Huntington disease. Depletion of FUS/TLS by sequestration in aggregates may contribute to neuronal cell death in polyglutamine-expansion-mediated diseases; loss of function of FUS/TLS in recessive cases of motor neuron disease may mimic this pathology (of note, CBP, one binding partner of FUS/TLS, also contains a polyglutamine tract).

Unexpectedly, several mutations have been found in the sequence of the FUS/TLS gene in ALS patients (both familial ALS and sporadic ALS). The numbering of the sequence starts with the A of the start codon as base 1 and intronic bases relative to the nearest exon, plus or minus).

Familial ALS (FALS):

| DNA change | location/aa change | other |
|---|---|---|
| Exon 15: | | |
| GG1542-3TT | R514S/G515C | [cis and/or trans] possible splicing change |
| C1551G | H517Q | (Family 577)[1] |
| C1561T | R521C | |
| C1561G | R521G | (Family 55)[2] |
| G1562A | R521H | |
| G1562T | R521L | |
| A1564G | R522G | |
| G1572C | R524S | |
| C1574G | P525R | |
| T-C | 3'UTR +22 | possible RNA stability change |
| T-C | 1542IVS-8 | possible splicing change |
| Exon 3: | | |
| G66A | G22G (silent) | |
| C58T | Q20X | |
| Exon 5: | | |
| T196C | Y155H | |
| Intron 8: | | |
| C-T @ IVS833-11 | | possible splicing change |
| Intron 11: | | |
| A-G @ IVS1067-11 | | possible splicing change |
| Sporadic ALS (SALS): | | |
| exon 15 G-C | Q519C | |

[1]Family 577 is a multigenerational pedigree segregating ALS as a pseudo-dominant trait, believed to be recessive [family contains at least one consanguineous loop]; the most significant region of identity-by-descent in affected individuals is on chromosome 16. Affecteds have a non-bulbar (thus non-fatal) form of lower > upper motor neuron disease.
[2]Family 55 is a multigenerational pedigree segregating ALS as a dominant trait (linked to chromosome 16, reported by our group).

[1]Family 577 is a multigenerational pedigree segregating ALS as a pseudo-dominant trait, believed to be recessive [family contains at least one consanguineous loop]; the most significant region of identity-by-descent in affected individuals is on chromosome 16. Affecteds have a non-bulbar (thus non-fatal) form of lower>upper motor neuron disease.
[2]Family 55 is a multigenerational pedigree segregating ALS as a dominant trait (linked to chromosome 16, reported by our group).

One family may segregate both X-linked spinobulbar muscular atrophy and FUS/TLS-mediated motor neuron disease.

The term "allele" is used herein to refer to variants of a nucleotide sequence. A biallelic polymorphism has two forms. Typically the first identified allele is designated as the original allele whereas other alleles are designated as alternative alleles. Diploid organisms are homozygous or heterozygous for an allelic form.

The term "genotype" as used herein refers the identity of the alleles present in an individual or a sample. The term "genotyping" a sample or an individual for an allelic marker consists of determining the specific allele or the specific nucleotide carried by an individual at an allelic marker.

The term "haplotype" refers to a combination of alleles present in an individual or a sample.

The methods described herein relate to the detection of SNP markers. As used herein, the term "SNP" includes all single base variants and also includes single nucleotide insertions and deletions in addition to single nucleotide substitutions (e.g., A→G). A single nucleotide polymorphism occurs at a polymorphic site occupied by a single nucleotide, which is the site of variation between allelic sequences. The typical frequency at which SNPs are observed is about 1 per 1000 base pairs (Li and Sadler, Genetics, 129:513-523, 1991; Wang et al., Science, 280:

1077-1082, 1998; Harding et al., Am. J. Human Genet., 60:772-789, 1997; Taillon-Miller et al., Genome Res., 8:748-754, 1998).

Typically, between different genomes or between different individuals, the polymorphic site is occupied by two different nucleotides. SNPs occur at defined positions within genomes and can be used for gene mapping, defining population structure, and performing functional studies. SNPs are useful as markers because many known genetic diseases are caused by point mutations and insertions/deletions. The conformation of the nucleic acid molecule is generally detectable, identifiable and/or distinguishable using methods known in the art, such as electrophoretic mobility as measured by gel electrophoresis, capillary electrophoresis, and/or susceptibility to endonuclease digestion etc.

"Linkage" describes the tendency of genes, alleles, loci or genetic markers to be inherited together as a result of their location on the same chromosome, and can be measured by percent recombination between the two genes, alleles, loci or genetic markers. Loci occurring within 50 centimorgan of each other are linked. Some linked markers occur within the same gene or gene cluster.

"Linkage disequilibrium" or "allelic association" means the preferential association of a particular allele or genetic marker with a specific allele, or genetic marker at a nearby chromosomal location more frequently than expected by chance for any particular allele frequency in the population. Linkage disequilibrium may result from natural selection of certain combination of alleles or because an allele has been introduced into a population too recently/to have reached equilibrium with linked alleles.

"Genetic variant" or "variant" means a specific genetic variant which is present at a particular genetic locus in at least one individual in a population and that differs from a reference sequence.

The genetic material to be assessed can be obtained from any nucleated cell from the individual. The nucleic acids used in the methods according to the present invention can be DNA, genomic DNA, RNA, cDNA, hnRNA and/or mRNA. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from the central nervous system or brain are suitable sources for obtaining cDNA for the FUS/TLS gene.

Applicable diagnostic techniques include, but are not limited to, DNA sequencing including mini-sequencing, primer extension, hybridization with allele-specific oligonucleotides, oligonucleotide ligation assays, PCR using allele-specific primers, dot blot analysis, flap probe cleavage approaches, restriction fragment length polymorphism, kinetic PCR, and PCR-SSCP, fluorescent in situ hybridisation, pulsed field gel electrophoresis analysis, Southern blot analysis, single stranded conformation analysis, denaturing gradient gel electrophoresis, temperature gradient gel electrophoresis, denaturing HPLC and RNAse protection assays, all of which are presently known to the person skilled in the art and routinely practiced in the art.

Many of the methods described herein require amplification of DNA from target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotides which occupy the polymorphic sites of interest can be identified by a variety methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE); A sampling of suitable procedures are discussed below.

The design and use of allele-specific probes for analyzing polymorphisms is described by e.g., Saiki et al., Nature 324, 163-166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-50° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

The polymorphisms can also be identified by hybridization to nucleic acid arrays (e.g., microarrays), some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

An allele-specific primer hybridizes to a site on target DNA overlapping a polymorphism and only primes amplification of an allelic form to which the primer exhibits perfect complementarity. See Gibbs, Nucleic Acid Res. 17, 2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

The direct analysis of the sequence of polymorphisms of the present invention can be accomplished using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (PNAS 94:10756-61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

A polymorphism may be one of a group of two or more polymorphisms in the FUS/TLS gene, or in linkage disequilibrium with such polymorphisms, that form a haplotype which contributes to the presence, absence or severity of ALS or other related motor neuron disease. An assessment of other polymorphisms within the FUS/TLS gene, or in linkage disequilibrium with such polymorphisms, can be undertaken, and the separate and combined effects of these polymorphisms on the patient's phenotype can be assessed.

Correlation between a particular phenotype and the presence or absence of a particular allele is performed for a population of individuals who have been tested for the presence or absence of the phenotype. Correlation can be performed by standard statistical methods as known in the art and as described herein and statistically significant correlations between polymorphic form(s) and phenotypic characteristics are noted.

Furthermore, it may be possible to identify a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., Proc. Natl. Acad. Sci. (USA) 83, 7353-7357 (1986); Lander et al., Proc. Natl. Acad. Sci. (USA) 84, 2363-2367 (1987); Donis-Keller et al., Cell 51, 319-337 (1987); Lander et al., Genetics 121, 185-199 (1989)). Genes localized by linkage can be cloned by a process known as directional cloning. See Wainwright, Med. J. Australia 159, 170-174 (1993); Collins, Nature Genetics 1, 3-6 (1992).

Individuals diagnosed according to the methods of the invention as having an above-normal likelihood of having or developing ALS or other related motor neuron disease may also be treated with compounds that modulate FUS/TLS function or activity. The modulator treatment can be provided alone or in combination with other known treatment modalities for ALS and related motor neuron diseases. One possible modulator is an inhibitor molecule that inhibits the function of mutant FUS/TLS (i.e., FUS/TLS comprising one or more of the mutations provided by the invention) or reduces expression of mutant FUS/TLS (i.e., FUS/TLS comprising one or more of the mutations provided by the invention), such as a siRNA or antisense molecule. In one particular embodiment, the inhibitor is an antisense oligonucleotide or siRNA molecule that selectively binds to a mutant FUS/TLS nucleic acid molecule, to reduce the expression of the encoded mutant FUS/TLS gene product in a cell.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

As used herein, a "siRNA molecule" is a double stranded RNA molecule (dsRNA) consisting of a sense and an antisense strand, which are complementary (Tuschl, T. et al., 1999, Genes & Dev., 13:3191-3197; Elbashir, S. M. et al., 2001, EMBO J., 20:6877-6888). In one embodiment the last nucleotide at the 3' end of the antisense strand may be any nucleotide and is not required to be complementary to the region of the target gene. The siRNA molecule may be 19-23 nucleotides in length in some embodiments. In other embodiments, the siRNA is longer but forms a hairpin structure of 19-23 nucleotides in length. In still other embodiments, the siRNA is formed in the cell by digestion of double stranded RNA molecule that is longer than 19-23 nucleotides. The siRNA molecule preferably includes an overhang on one or both ends, preferably a 3' overhang, and more preferably a two nucleotide 3' overhang on the sense strand. In another preferred embodiment, the two nucleotide overhang is thymidine-thymidine (TT). The siRNA molecule corresponds to at least a portion of the mutant FUS/TLS gene of interest. In a preferred embodiment the first nucleotide of the siRNA molecule is a purine. Many variations of siRNA and other double stranded RNA molecules useful for RNAi inhibition of gene expression will be known to one of ordinary skill in the art.

The siRNA molecules can be plasmid-based. In a preferred method, a polypeptide encoding sequence of the mutant FUS/TLS gene is amplified using the well known technique of polymerase chain reaction (PCR). The use of the entire polypeptide encoding sequence is not necessary; as is well known in the art, a portion of the polypeptide encoding sequence is sufficient for RNA interference. For example, the PCR fragment can be inserted into a vector using routine techniques well known to those of skill in the art. The insert can be placed between two promoters oriented in opposite directions, such that two complementary RNA molecules are produced that hybridize to form the siRNA molecule. Alternatively, the siRNA molecule is synthesized as a single RNA molecule that self-hybridizes to form a siRNA duplex, preferably with a non-hybridizing sequence that forms a "loop" between the hybridizing sequences. Preferably the nucleotide encoding sequence is part of the coding sequence of the mutant FUS/TLS gene. The siRNA can be expressed from a vector introduced into cells.

Vectors comprising the mutant FUS/TLS gene sequences are provided for production of siRNA, preferably vectors that include promoters active in mammalian cells. Non-limiting examples of vectors are the pSUPER RNAi series of vectors (Brummelkamp, T. R. et al., 2002, Science, 296:550-553; available commercially from OligoEngine, Inc., Seattle, WA). In one embodiment a partially self-complementary nucleotide coding sequence can be inserted into the mammalian vector using restriction sites, creating a stem-loop structure. In a preferred embodiment, the mammalian vector comprises the polymerase-III H1-RNA gene promoter. The polymerase-III H1-RNA promoter produces a RNA transcript lacking a polyadenosine tail and has a well-defined start of transcription and a termination signal consisting of five thymidines (T5) in a row. The cleavage of the transcript at the termination site occurs after the second uridine and yields a transcript resembling the ends of synthetic siRNAs containing two 3' overhanging T or U nucleotides. Other promoters useful in siRNA vectors will be known to one of ordinary skill in the art.

Vector systems for siRNA expression in mammalian cells include pSUPER RNAi system described above. Other examples include but are not limited to pSUPER.neo, pSUPER.neo+gfp and pSUPER.puro (OligoEngine, Inc.); BLOCK-iT T7-TOPO linker, pcDNA1.2/V5-GW/lacZ, pENTR/U6, pLenti6-GW/U6-laminshrna and pLenti6/BLOCK-iT-DEST (Invitrogen). These vectors and others are available from commercial suppliers.

It is preferred that the antisense oligonucleotide or siRNA molecule be constructed and arranged so as to bind selectively with the target under physiological conditions, i.e., to hybridize substantially more to the target sequence than to any other sequence in the target cell under physiological conditions. One of skill in the art can easily choose and synthesize any of a number of appropriate antisense or siRNA molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840-844, 1996). Most preferably, the antisense oligonucleotides comprise a complementary sequence of 20-30 bases. For siRNA molecules, it is preferred that the molecules be 21-23 nucleotides in length, with a 3' 2 nucleotide overhang, although shorter and longer molecules and molecules without overhangs are also contemplated as useful in accordance with the invention.

The antisense is targeted, preferably, to sites in which mRNA secondary structure is not expected (see, e.g., Sainio et al., *Cell Mol. Neurobiol.* 14(5): 439-457, 1994) and at which polypeptides are not expected to bind. Other methods for selecting preferred siRNA sequences are known to those of skill in the art (e.g., the "siRNA Selection Program" of the Whitehead Institute for Biomedical Research (2003)).

In one set of embodiments, the antisense oligonucleotides or siRNA molecules of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors, including in situ.

In preferred embodiments, however, the antisense oligonucleotides or siRNA molecules of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, the mutant FUS/TLS gene, together with pharmaceutically acceptable carriers.

Another possible modulator is an expression vector that expresses functional FUS/TLS protein, by which FUS/TLS activity is increased. Suitable expression vectors are well known in the art, as are techniques for constructing, producing and administering recombinant expression vectors in order to express a protein, in this case FUS/TLS.

The invention is also directed to a diagnostic kit and/or a research kit that comprises at least one probe for detecting the FUS/TLS SNPs that are markers for and indicative of ALS and other related motor neuron diseases according to the present invention. The kit can contain other compounds such as enzymes, buffers, and/or dyes for performing the method(s) of the present invention. The kit can also include instructions for performing the SNP-analysis and/or the software for a statistical analysis as described herein.

Preferably the invention further provides kits comprising at least one allele-specific oligonucleotide as described herein. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting any one or more of the polymorphisms disclosed herein. Optional additional components of the kit include, for example, restriction enzymes, reverse-transcriptase or polymerase, the substrate nucleoside triphosphates, means used to label, and the appropriate buffers for reverse transcription, PCR, or hybridization reactions. Usually, the kit also contains instructions for carrying out the methods.

The invention further provides efficient methods of identifying pharmacological agents or lead compounds for agents and molecules that reduce mutant FUS/TLS activity. Generally, the screening methods involve assaying for compounds which modulate the amount of activity of mutant FUS/TLS. As will be understood by one of ordinary skill in the art, the screening methods may measure the amount of activity directly, by using methods well known in the art. In addition, screening methods may be utilized that measure a secondary effect of mutant FUS/TLS activity.

A wide variety of assays for pharmacological agents can be used in accordance with this aspect of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents useful in accordance with the invention encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Biopsy cells and tissues as well as cell lines grown in culture are useful in the methods of the invention.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the activity of mutant FUS/TLS is detected by any convenient method available to the user. For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens, such as reporter gene transcription as described in the Examples below. For cell-free binding assays, at least one of the components usually comprises, or is coupled to, a detectable label. A wide variety of labels can be used, such as those that provide direct detection (e.g., radioactivity, luminescence, optical or electron density, energy transfer, etc.) or indirect detection (e.g., epitope tag such as the FLAG or myc epitopes, enzyme tag such as horseradish peroxidase, etc.).

A variety of methods may be used to detect the label, depending on the nature of the label and other assay components. For example, the label may be detected while bound to the solid substrate or subsequent to any separation from the solid substrate. Labels may be directly detected through optical or electron density, radioactive emissions, nonradiative energy transfers, etc. or indirectly detected with antibody conjugates, strepavidin-biotin conjugates, etc. A variety of methods for detecting the labels are well known in the art.

The present invention is described in further detail in the following non-limiting Examples.

EXAMPLES

Amyotrophic lateral sclerosis (ALS) is a fatal degenerative disorder of upper and lower motor neurons. ALS is predominantly sporadic in occurrence, although 10% of cases are familial, segregation is typically autosomal dominant although many small familial clusters are observed with unclear mode of inheritance. Most familial cases, though, involve as-yet unidentified genes. We identified several different mutations in the FUS/TLS gene associated with autosomal dominant ALS as well as a unique mutation associated with a rare, recessive, non-fatal ALS variant. The cognate protein is widely expressed and is found in both the nucleus and cytoplasm. FUS/TLS is involved with several cellular processes, particularly with mRNA splicing and transport. Mutant forms of FUS/TLS still bind RNA but accumulate in clumps in the cytoplasm of cells in vitro; patient brain and spinal cord likewise show cytoplasmic FUS/TLS retention as well as nuclear ubiquitin staining. These results suggest a role for RNA processing and/or transport in ALS.

Materials and Methods

Loss-of-Heterozygosity mapping. DNA samples were amplified and hybridized to 250k (Sty I) SNP microarrays (Affymetrix) at the TGEN genomics core facility. Genotype data were analyzed using autoSNPa software and graphically visualized using the IBD ("identical by descent") module, using a 20-SNP-run cutoff and selecting for regions homozygous in all 3 F577 patients.

PCR and Sequencing. Human (patient, family members, and controls) FUS/TLS sequences were obtained by PCR amplification with M13 forward and reverse-tailed primers, Exonuclease I/Shrimp alkaline phosphatase treatment, and direct sequencing. DNA samples were extracted from lymphoblastoid cell lines or whole blood; some of the latter were amplified with a Genomiphi kit (GE Healthcare Lifesciences). For screening of candidate gene exons, primers were designed using the UCSC genome browser, targeting coding sequences and 60 bp flanking regions; primer pairs failing PCR amplification were redesigned using the Whitehead Institute Primer3 software. For FUS/TLS gene sequencing, primer sequences were as follows:

Cloning. A full-length human FUS/TLS cDNA, MGC-8537, (In Vitrogen) was obtained (in pOTB7) and the insert was cloned into pcDNA3.2V5 (Invitrogen) by att site recombination using pDONR221 as the entry vector and the BP and LR Clonase kits (In Vitrogen). Mutations corresponding to F55 and F577 patients were introduced using a QuikChange II Site-Directed Mutagenesis kit (Stratagene). Mutations were confirmed by sequencing.

Extraneous pOTB7 sequences and cDNA 5' UTR sequences were removed by amplification with attB-site-tailed primers (so as to avoid addition of extra N-terminal amino acids after the N-terminal tag) into pcDEST53 and pcDEST17 (In Vitrogen), via pDONR221, as above.

Mutations were confirmed by sequencing; additionally, the pcDEST53 plasmids were sequenced in their entirety.

Cell Culture. Human neuroblastoma SKNAS cells were cultured in Dulbecco's modified Eagle's medium (DMEM) supplemented with 10% fetal bovine serum (FBS) and 4 mM L-glutamine. Murine neuroblastoma N2A cells were cultured in minimal essential medium (MEM) containing 10% FBS, 4 mM L-glutamine, and 1 mM sodium pyruvate. Cells were maintained in a humidified 10% $CO_2$ chamber at 37° C. All tissue culture reagents were purchased from Gibco (Invitrogen).

Transfection of mammalian cells with GFP-FUS plasmids. For fluorescence microscopy, $7.5\times10^4$ SKNAS cells/well or $1.0\times10^5$ N2A cells/well per were plated in 24-well dishes and allowed to adhere to poly-L-lysine coated glass coverslips (BD Biosciences) for ~14 h. The media was then replaced with OPTI-MEM containing 800 ng plasmid DNA and 1.25 μL Lipofectamine 2000 reagent according to the manufacture's instructions (Invitrogen). After 5 h, the media was replaced with the respective serum-containing medium.

Transfections were allowed to proceed for a total of 24 h. Cells grown on coverslips were then thoroughly rinsed with phosphate buffered saline (PBS), fixed with 3% paraformaldehyde for 15 min, and adhered onto glass slides with Vectashield hard mount containing DAPI (Vectorlabs). Transfection of SKNAS cells for subcellular fractionation experiments was performed as described above except that $2.2\times10^6$ cells were plated in 10 cm dishes with 16 μg plasmid DNA and 25 μL Lipofectamine 2000 reagent.

Quantification of Cytosolic versus Nuclear GFP-FUS/TLS in transfected cells. SKNAS and N2A cells transfected with either GFP-FUS (WT), GFP-FUS (55), or GFP-FUS (577) were visualized with a Nikon TE300 inverted fluorescence microscope at 100× magnification. Detection of green fluorescence outside the nuclear compartment boundary (identified with DAPI stain) was determined to represent cytosolic GFP-FUS expression. A minimum of 150 cells on three coverslips prepared from at least 2 independent transfection experiments were categorized as having GFP-FUS expression localized only to the nucleus, or having cytosolic GFP-FUS expression (the latter category includes cells having both nuclear and cytosolic GFP-FUS expression). Results are presented as the mean percentage of total cells counted, and analyzed with Holm test statistics.

SKNAS cells transfected with either GFP-FUS (WT), GFP-FUS (55), or GFP-FUS (577) were subjected to subcellular fractionation using the Qproteome cell compartment kit (Qiagen) according to the manufacture's instructions. Cell pellets from each fraction, including the insoluble fraction, were re-suspended in PBS containing 2% sodium dodecyl sulfate (SDS) and 1% triton X-100, and the total protein concentration from all fractions was quantified with the bicinchoninic acid (BCA) assay (Pierce). 3 μg total protein from the cytosolic and nuclear fractions, and 1.25 μg total protein from the insoluble fractions were subjected to Western blot analysis. GAPDH (1:2000; Abcam) and Lamin A/C (1:3000; BD Transduction laboratories) served as loading standards as well as cytosolic and nuclear compartment markers, respectively. GFP-FUS proteins were detected with the living colors A.v. monoclonal (anti-GFP) antibody JL-8 (1:4000; Clontech). The ratio of cytosolic/nuclear and insoluble/nuclear FUS was quantified from the densitometry of three Western blots, and analyzed with Holm test statistics.

Immunohistochemistry. Fifteen micron sections were taken from frontal cortex, fixed in 4% paraformaldehyde for 10 minutes and washed three times for five minutes each with PBS. Sections were then blocked (20% normal goat serum/0.1% Triton X/PBS) for 1 hour at room temperature, then incubated with primary antibodies overnight at 4° C.: rabbit polyclonal anti-ubiquitin (1:600, Abcam) and mouse anti-FUS/TLS (Santa Cruz Labs, 1:50) or mouse monoclonal anti-NeuN (1:1000 Chemicon) and rabbit anti-Fus (Bethyl Labs, 1:500). Sections were washed three times with PBS for 5 minutes each, then incubated with secondary antibodies for 3 hours at room temperature: goat anti-rabbit fluorescein isothiocyanate (Jackson Immuno, 1:200) and goat anti-mouse Cyanine3 (Jackson Immuno, 1:300). Sections were washed as above, then incubated in 70% ethanol for 5 minutes followed by incubation with autofluorescence elimininator reagent (Chemicon) for 4 minutes and washed in 70% ethanol for 1 minute. Sections were counterstained and mounted with Vectashield hard mounting medium with DAPI (Vector Labs).

Results

Two large families segregating ALS in an autosomal dominant manner, with linkage to chromosome 16, have previously been reported. Haplotype analyses in these pedigrees demonstrated a 40 Mb candidate region for this locus. Two additional families displayed linkage to a smaller region comprising a telomeric subset of this locus, leading us to focus efforts on this area. Exhaustive exon sequencing revealed no mutation not also seen in controls. Subsequently, ascertainment of additional individuals and reanalysis of data for these two families excluded linkage to chromosome 16.

Recently we observed a kindred segregating an atypical ALS phenotype in a pseudo-autosomal fashion (FIG. 1A). The phenotype consists of proximal upper extremity onset weakness with subsequent spread to lower extremities but sparing the bulbar region in all four patients; upper motor neuron signs were present, though minimal, in the two probands indicated. Muscle atrophy was present is all cases but much less than expected for near-total paresis. The mother of these probands lived 14 years from onset without developing bulbar symptoms (though quadraparetic) and reportedly died of a myocardial infarction. The maternal grandparents of the proband were first cousins; additionally, the family originates from a small island of roughly 6000 inhabitants, raising the possibility that the proband's father and mother are related as well. This would allow for a recessive mode of inheritance. Loss-of-heterozygosity mapping using 250k SNP chips and the autoSNPa software identified a major LOH cluster in the pericentromeric region of chromosome 16 constituting a subset of the previously reported locus, as well as a few smaller regions elsewhere.

Figure 1B:
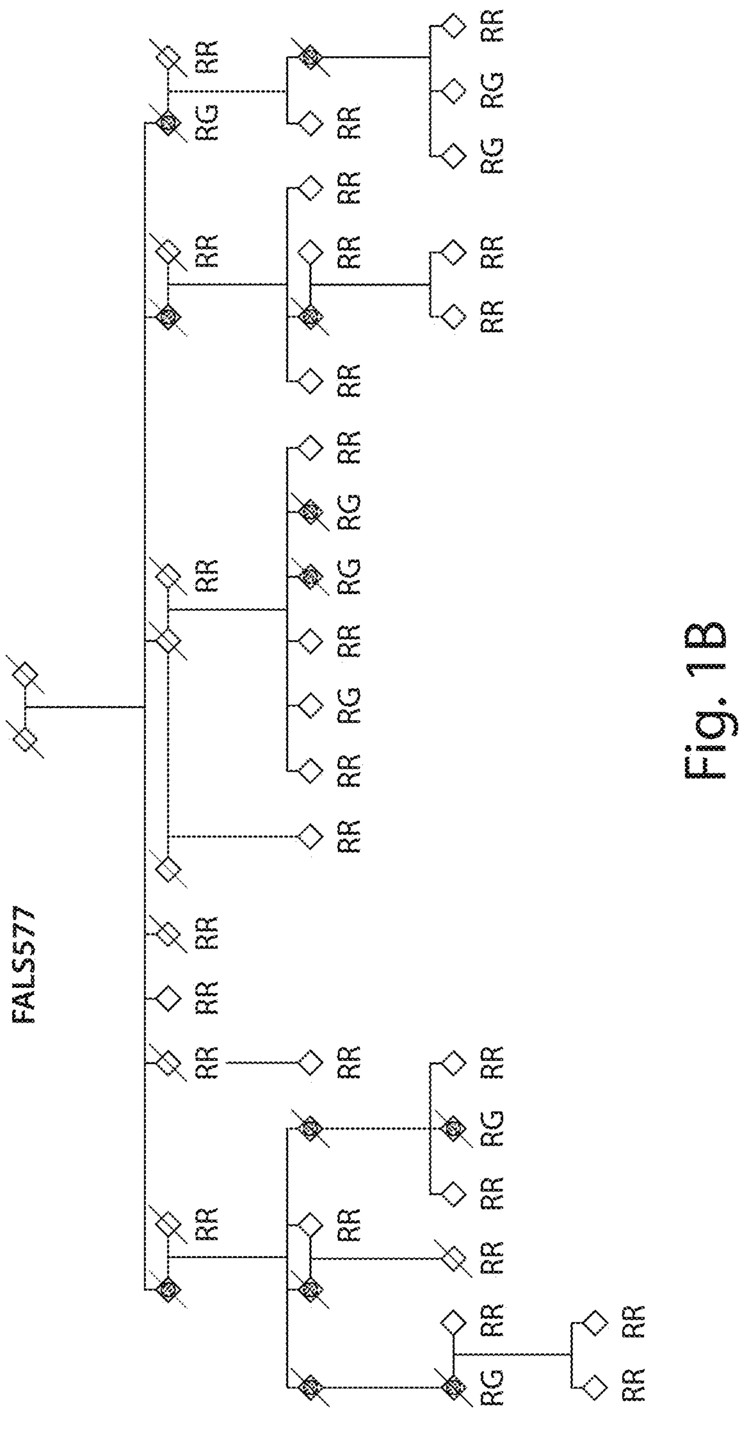

The largest contiguous LOH cluster comprised approximately 4 Mb and contained 53 genes comprising 315 coding exons. Genomic sequencing of approximately 75% of these exons was performed, prioritizing according to estimated importance in neuronal function. Sequence variants were discovered in patients from both pedigrees in exon 15 of the FUS/TLS (fusion protein/translocated in liposarcoma) gene. In family 55, all five available affected individuals were shown to be heterozygous for a C1561G mutation causing an R521G substitution (FIG. 1B), while all 3 available patients from family 577 were shown to be homozygous for a C1551G mutation resulting in a H517Q substitution (FIG. 1A). Screening of index cases from 120 additional familial ALS pedigrees for all 15 exons has revealed seven other mis-sense mutations in exon 15; screening of 293 sporadic ALS cases for exon 15 has revealed no mutations. Additional variants of uncertain significance were observed, including a silent coding mutation, three intronic variants, and a 3' UTR variant. None of the exon 15 variants was observed in 795 control individuals sequenced. All sequence variants in other genes in this region were either previously reported in online SNP databases or were detected in multiple control samples.

Figure 2A:
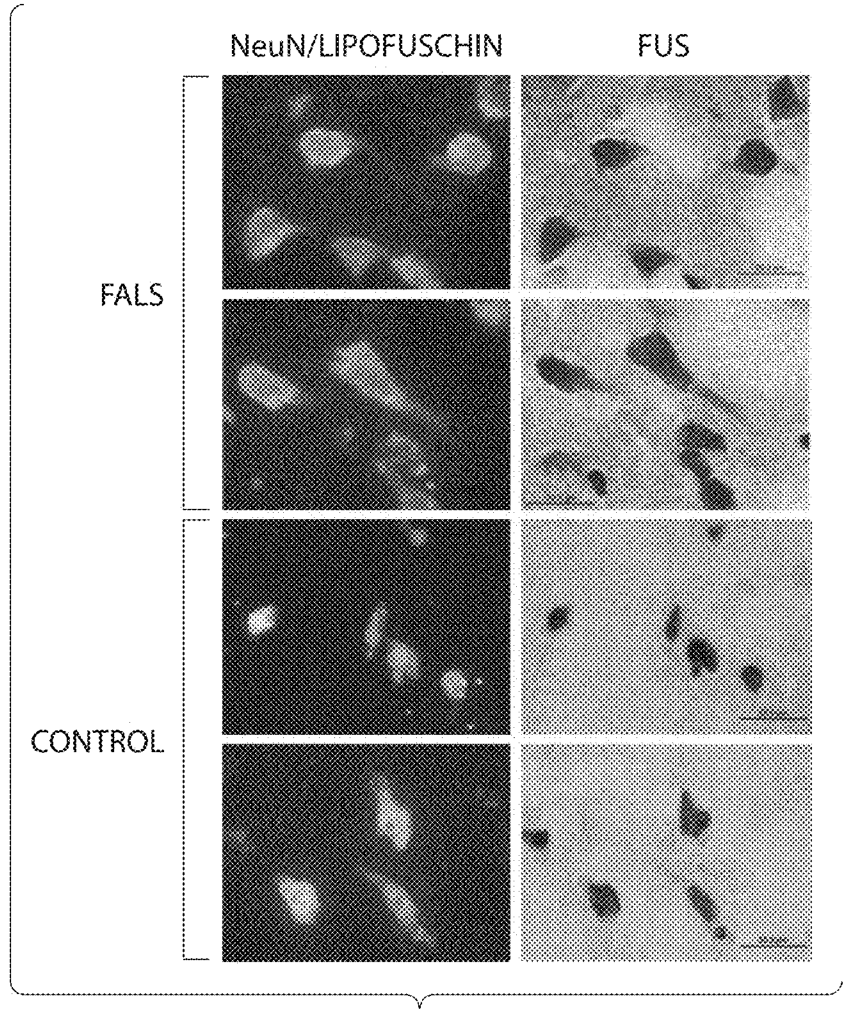
FIGS. 2A-2B: FUS/TLS tissue and cell staining and RNA binding.
Figure 2B:
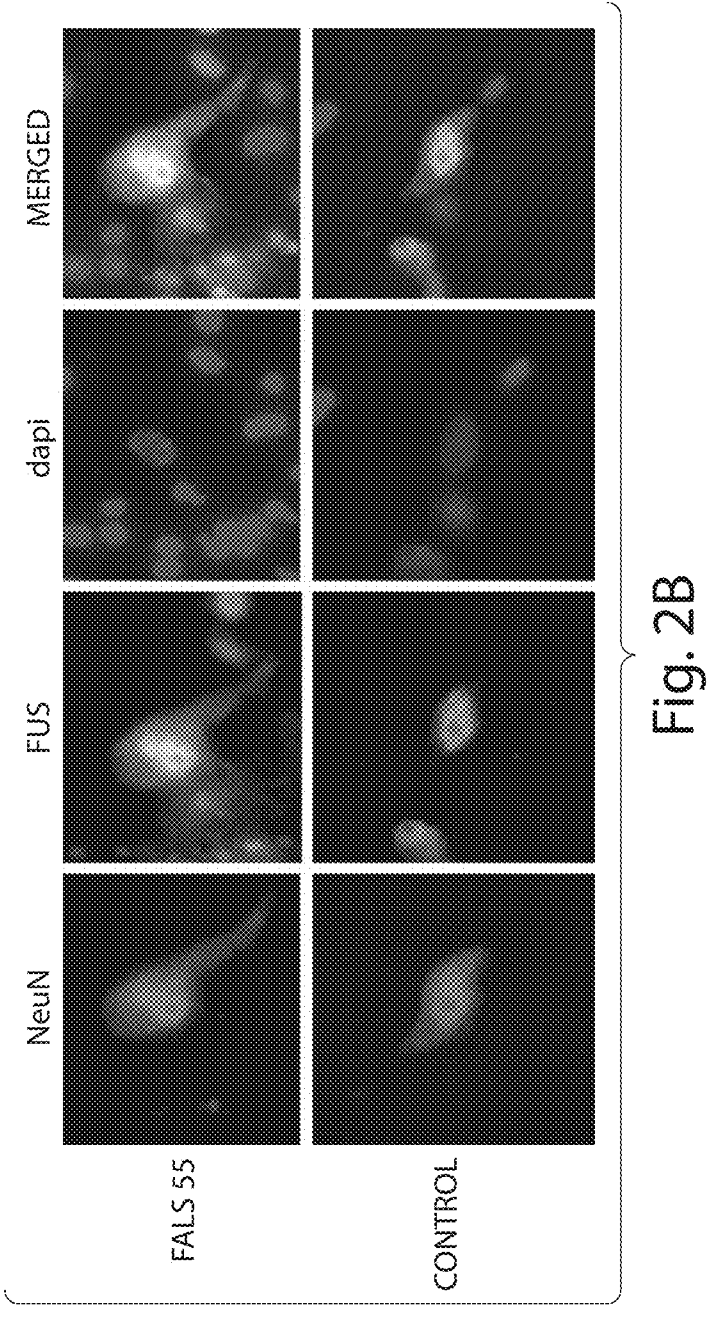

Autopsy tissue from a single patient from family 55 (F55) was available. Routine pathologic examination findings included loss of motor neurons in the anterior horn of the spinal cord at multiple levels and in the hypoglossal nucleus, myelin pallor in the anterior corticospinal tracts and macrophage aggregates replacing Betz cells in the motor cortex. Frozen brain tissue was subsequently examined by immunohistochemistry. Both control and patient tissue show clear cortical neuronal FUS/TLS staining, but whereas predominantly nuclear staining was observed in control tissue, F55 patient tissue (heterozygous for the R521G mutation) showed prominent cytoplasmic staining as well (FIG. 2A). Further staining with an anti-ubiquitin antibody revealed diffuse nuclear staining in the patient's tissue but not control tissue (FIG. 2B). There was increased lipofuschin staining in patient neurons compared to control neurons, consistent with increased accumulation of cellular debris in ALS neurons.

FUS/TLS wild-type, R521G, and H517Q cDNA expression constructs were prepared in pcDNA3.2 (Invitrogen-untagged), pcDEST53 (Invitrogen-N-terminal gfp-tagged), and pcDEST17 (Invitrogen-N-terminal His-tagged). RNA-binding experiments were performed with His-tagged, purified protein produced in *E. Coli* and RNA 24-mer oligos containing GGUG motifs and known to bind FUS/TLS. Mutant forms of FUS/TLS (the recessive H517Q and dominant R521C) both bind RNA oligomers in a gel-shift assay in a manner similar to wild-type protein. Transfection of SK-NAS neuronal cells and N2A neuronal cells with gfp-tagged FUS/TLS constructs revealed cytoplasmic accumulation of mutant FUS/TLS protein by 24 hours, stronger for R521G than for H517Q (and absent in wild-type). This was also seen with untagged protein visualized with anti-FUS/TLS antibody and fluorescent secondary antibody (data not shown).

Figure 3A:
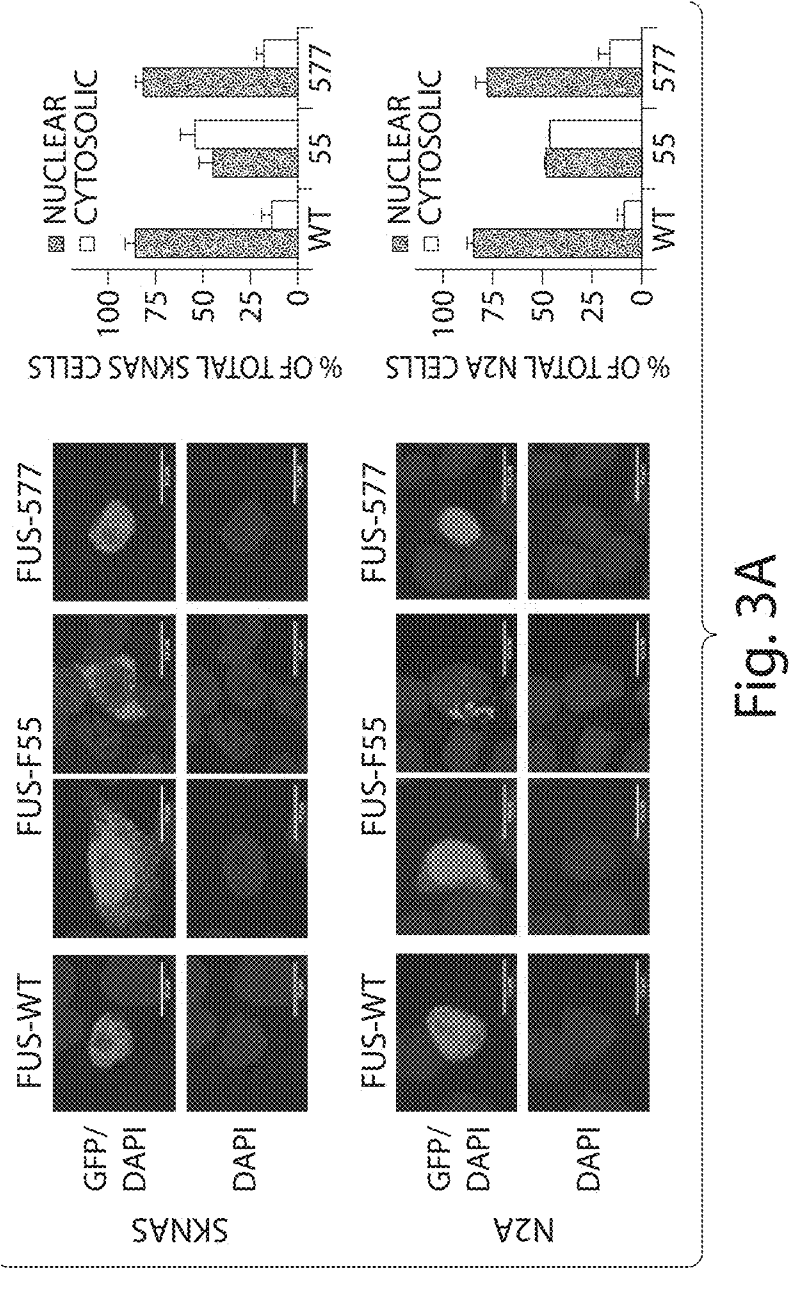
FIGS. 3A-B: Transfection and cell fractionation studies.
Figure 3B:
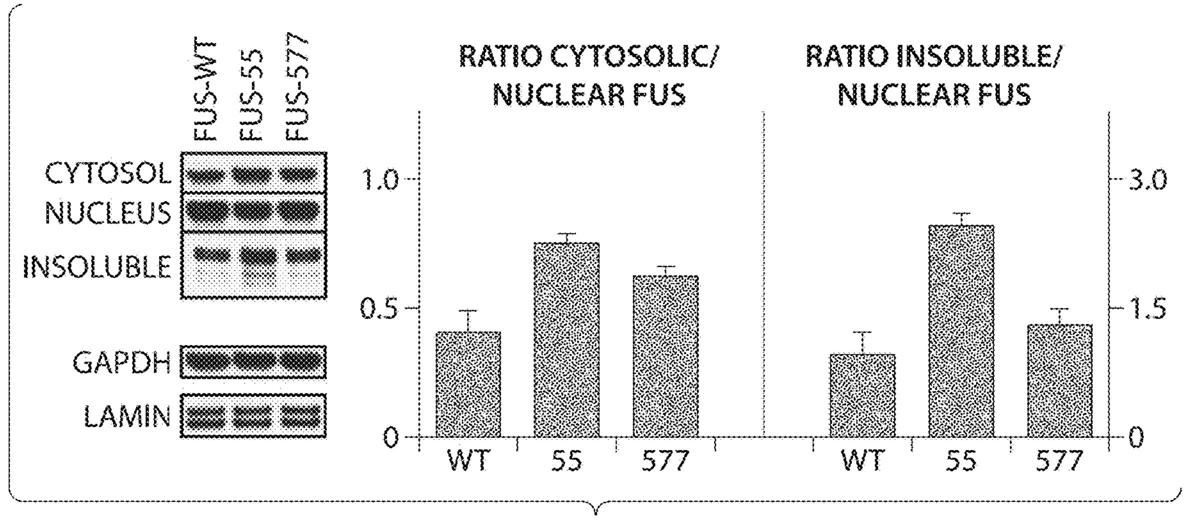

Subcellular localization of FUS/TLS was examined by compartmental fractionation of SKNAS cells transfected with wild-type, R521G, or H517Q FUS/TLS-GFP fusion proteins. Western blotting of fractions followed by immunostaining with an anti-GFP antibody demonstrate a substantially higher cytosol: nuclear FUS/TLS signal for both mutants (FIG. 3B). Additionally, a higher ratio of insoluble to nuclear FUS/TLS protein is seen for the R521G mutant than for controls, while the ratio is only slightly increased for H517Q mutant FUS/TLS protein.

DISCUSSION

FUS/TLS was originally described as contributing the N-terminal half of a fusion protein created by somatic chromosomal translocations in liposarcoma. It has since been shown to have roles in DNA repair, RNA processing and transport. FUS/TLS knock-out mice display a variable phenotype, depending on strain background, with either perinatal mortality or male sterility and radiation sensitivity. Neuronal dysfunction has not been described, though no long-term studies of mouse neuronal function have been published. A recent report shows that noncoding RNAs bind FUS/TLS protein, enabling it to associate with CREB-binding protein (CBP) and inhibit the latter's histone-acetyltransferase activity, leading to inhibition of transcription. This activation of FUS/TLS binding by GGUG-containing ncRNAs appears to act by preventing association of the N- and C-terminal regions of FUS/TLS. It is tempting to speculate that mutations in arginine residues in the C-terminal region of FUS/TLS, such as those seen in dominantly-inherited ALS patients, could also prevent this self-association and lead to a constitutively-active transcription repressor. Also, FUS/TLS has been found to be a major nuclear-aggregate-interacting protein in a model of Huntington disease. It is tempting to speculate that depletion of FUS/TLS by sequestration in aggregates may contribute to neuronal cell death in polyglutamine-expansion-mediated diseases; loss of function of FUS/TLS in recessive cases of motor neuron disease may mimic this pathology (of note, CBP, one binding partner of FUS/TLS, also contains a polyglutamine tract).

A neuronal function for FUS/TLS has been delineated in hippocampal neuronal slice culture—the protein is found in RNA granules that are transported to dendritic spines in response to metabotropic (mGluR1) glutamatergic stimulation. These granules contain a number of proteins (including TDP-43) and mRNA species, including actin and an actin-stabilizing protein. Indeed, FUS/TLS deficient neurons show decreased spine arborization with abnormal morphology.

Two mutations (one dominant, one recessive) associated with motor neuron disease appear to cause abnormal accumulation of FUS/TLS in the cytoplasm of neuronal cells in culture—the dominant mutation to a greater degree. Such sequestration may lead to cellular dysfunction via a reduction in the amount of protein available in the nucleus or by a toxic gain of function in the cytoplasm. It is also possible that mutant FUS/TLS may be incorporated into RNA granules but not function properly in delivery of mRNA to dendritic spines, thus exerting either a dominant negative effect, or, in the case of the recessive mutation, through a partial loss of function. The presence of TDP-43 and FUS/TLS, two ALS-associated proteins, in the same RNA granule suggests that perturbations in the structure or localization of these granules may be important in the pathogenesis of motor neuron disease, at least in cases related to these two genes.

TABLE 1

FUS/TLS mutations with cognate phenotype data for ALS cases. Base numbering begins with the start codon; amino acid numbering begins with the start codon methionine.

| | Mutation | | Age onset (yrs) | | Duration (mos) | | # positive FALS Pedigrees |
|---|---|---|---|---|---|---|---|
| ID No | Amino acid | Base Pair | Mean +/− S.D. | n | Mean +/− S.D. | n | (120 total)* |
| Index Pedigrees | | | | | | | |
| F577 | H517Q | H517Q/C1551G | 45 +/− 3.56 | 4 | 168 | 1 | 1 |
| F55 | R521G | R521G/C1561G | 39.6 +/− 13.3 | 13 | 26 +/− 16.5 | 13 | 1 |
| Other Cases | | | | | | | |
| F360 | R514S, G515C | G1542T, G1543T ** | 32.5 +/− 3.5 | 2 | 36 | 1 | 1 |
| F72 | R521C | C1561T | 35 +/− 14.8 | 3 | 26 +/− 8.2 | 3 | 1 |
| F67 | R521H | G1562A | 57.7 +/− 9.0 | 3 | 54 +/− 26.2 | 3 | 1 |
| F287 | R522G | A1564G | 28.5 +/− 14.8 | 2 | 25 +/− 15.6 | 2 | 1 |
| F346 | R524S | G1572C | 34 | 1 | 39 | 1 | 1 |
| | | Overall | 40.3 +/− 13.0 | 28 | 36.3 +/− 33.1 | 24 | 7 |
| | | All dominant (no F577) | 39.5 +/− 13.8 | 24 | 30.6 +/− 18.0 | 23 | 6 |

*No mutations were detected in DNA from 795 controls or 293 individuals with sporadic ALS.

** phase unknown

PCT Patent Application No. PCT/US89/02170 (WO 89/11548)

The present disclosure may be further understood in view of the following, which corresponds to the indicated sections of PCT Patent Application No. PCT/US89/02170 (WO 89/11548). The text is reproduced here verbatim.

WO 89/11548—Page 16 serves as an important tool for paternity testing. DNA typing can also be used to match biological evidence left at the scene of a crime with biological samples obtained from an individual suspected of committing the crime. In a similar fashion, DNA typing can be used to identify biological remains, whether those remains are a result of a crime or some non-criminal activity. The practice of forensic medicine now routinely involves the use of DNA probes, in protocols that can be made more efficient by employing the present invention.

To achieve the important and diverse benefits of the present invention, one must first synthesize the probes to be immobilized on a solid support. The probe sequence can be synthesized in the same manner as any oligonucleotide, and a variety of suitable synthetic methods were noted above in the discussion of PCR primers. The hybridizing region of the probes of the invention is typically about 10 to 50 nt in length, and more often 17 to 23 nt in length, but the exact length of the hybridizing region will of course depend on the purpose for which the probe is used. Often, for reasons apparent to those of skill in the art, the hybridizing region of the probe will be designed to possess exact complementarity with the target sequence to be detected, but once again, the degree of complementarity between probe and target is somewhat tangential to the present invention. The probes of the invention are, however, preferably "tailed" with an oligonucleotide sequence that plays a critical role in obtaining the benefits provided by the present invention.

This tail of the probes of the invention consists of ribonucleotides or deoxyribonucleotides (e.g., dT, dC, dG, and dA). The nucleotides of the tail can be attached to the hybridizing region of the probe with terminal deoxynucleotidyl transferase (TdT) by standard methods. In addition, the entire tailed probe can be synthesized by chemical methods, most conveniently by using a commercially available nucleic acid synthesizer. One can also synthesize the tails and hybridizing regions separately and then combine the two components. For instance, a preparation of tails can be prepared (and even attached to a solid support, such as a bead) and then attached to a preparation of hybridizing regions.

When using a DNA synthesizer to make the tailed probes of the invention, one should take steps to avoid making a significant percentage of molecules that, due to a premature chain termination event, do not contain a hybridizing region. One such step involves synthesizing the hybridizing region of the probe first, creating a tailed probe with.

PCT Patent Application No. PCT/US94/12305 (WO 95/11995)

The present disclosure may be further understood in view of the following, which corresponds to the indicated sections of PCT Patent Application No. PCT/US94/12305 (WO 95/11995). The text is reproduced here verbatim.

WO 95/11995—Page 27 substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6-30 nucleotides, and preferably from about 9-21 nucleotides. The two segments are often approximately the same length. Often, the probes (or segment of complementarity within probes) have an odd number of bases, so that an interrogation position can occur in the exact center of the probe.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nucleic acid probe comprising:

(a) a nucleotide sequence consisting of 25 to 30 contiguous nucleotides of SEQ ID NO: 3, or a complementary sequence thereof, including position 1562, except that the nucleotide at the position corresponding to position 1562 of SEQ ID NO: 3 is an A; and (b) a detectable label selected from the group consisting of a fluorescent label, a radioactive label, an optical or electron density label, an energy transfer label, an epitope tag, or an enzymatic label, wherein the nucleotide sequence is coupled to the detectable label.

2. A kit comprising the nucleic acid probe according to claim 1.

3. The kit of claim 2, wherein the nucleic acid probe is immobilized to a substrate.

4. A microarray comprising the nucleic acid probe according to claim 1.

* * * * *

```
                         SEQUENCE LISTING

<160> NUMBER OF SEQ ID NOS: 22

<210> SEQ ID NO 1
<211> LENGTH: 10115
<212> TYPE: DNA
<213> ORGANISM: Homo sapiens

<400> SEQUENCE: 1

aaaaaaagat aaaatgtcat cctcacatca gccttttgtt gtgaaaaata aaatcaagag      60

tttactcagt cagaacaggg cctgacagta agtcttgtta aagtgttagc tattacatat     120

tatagatgag cacaatgtat atcattatta aatgtcagct ttattattat tatttgtttt     180

gagacagtct tgctctgttg cccaggctgg agtgcagtgg cacgtcttgg ctcactgcaa     240

cttccgcctc ctgggttcaa gcgattctcc catctcagct tcctgagtag ctgggattac     300

agatgcgcgg acgacgcctg gctaattttt gtatttttag tagagacggg gtttcaccat     360

gttggccagg ctggtctcga actcctgacc tcgtgatcca cacgcctcgg cctcccaaag     420

tgctggtatt acaggcgtga gccaccgcac ccggtcagct ttattattaa atgttaactt     480

catctgcttt gtacacgaat gcatacccag tgcccagaac agtgcctgga acatactagg     540

tgctaaataa atatttgtga cttaatgcat gaataagggt ggacttcctt tcttttgctc     600

tcactggaga gttgaactct ccttccaaag gcggtggggt ggatattggc atattcaggg     660

cctttagggc tgaagtcaag ggcttagtgg ggcttaattt gtgggcgggc ccagggcatg     720

gccctcattg tttctctaga aagacgtgtc caaccctcaa aggaccttct gaaatcccgc     780
```

-continued tgaaaggtta agttgggaag gaaaacctgc atgcctatgt atcaggaatt aacgtctttt 840
gtcttgtttt attcagtagt ttcaaattgc cttctccagg caaggctgat gaaagtgcaa 900
gttgcaagtt aatttgaatg tttctttttg cttttgctct cacaggaagt gaaaaggcga 960
ccaaacactc tagcattcat gccaccaaaa agaggagtgt tttgcagtta caagacctgg 1020
attcgaatca cgactcctct tagctgccct gtaatcaggc acaattactt gggtctctga 1080
gtctcacttt ccttatctag aaaacggagg tatctttact tccttcgtaa gactgatgac 1140
aaggaaatta tctgtgcatt ttgaaaccac ttaagccttg tacacgtttt atttctggga 1200
tcgccctggt agggcttcag aaaaataaaa aggaggtccc tgagaaaagg ctgggtaccg 1260
tacatctgag gtcaaccctc tctggtccca aggatggcct gggctgttcc gccccgtggc 1320
tccccagggg caaagccatg aggatccggg tgagagccca gtgctggacg agcccggggc 1380
ccaggggtcc cggccgaaat ccctgctgtc tttcaggtca aacgtcataa tccccgaacc 1440
ccagaaaggc cgaaaggcaa ggcaaccctg aaagacgacg aagtcaacct cagggcgcag 1500
gagagggagg gccagtgtgc tgccgacgag ggaggctgga gccgcgggga cgaggcgccc 1560
catacagcgg caagagggtg gagggcagga gctcgccatc ctgggtgaaa gcggggccca 1620
gcgaaggggc ccggccacag gaatctcggt tccaccccgc tactcccggc tgtgactcca 1680
gtttcgtccc cagccgccgg gaccgccccc tcgccccgcc cccagcgggc actcaggccg 1740
taccactgtg ccttcatggg ggtggagata gatcgtgggc tagtcctgcc gaggagagag 1800
gggttcttcc tcaaaaaata tgattatgta tagtattcgc atgattctag ttaacttgtt 1860
tcccttctgc ctgctcggac cctctacctg ccctacgaag gggcggagt gcgttcctgc 1920 ctccccctgc tcttccgcgt ttggtgcgcg cctgcgcggt gcgtaggcgg cggagcgtac 1980
ttaagcttcg acgcaggagg gagagggagg gccagtgtgc tgccgacgag ggaggctgga 2040
gccgcgggga cgaggcgccc catacagcgg caagagggtg gagggcagga gctcgccatc 2100
ctgggtgaaa gcggggccca gcgaaggggc ccggccacag gaatctcggt tccaccccgc 2160
tactcccggc tgtgactcca gtttcgtccc cagccgccgg gaccgccccc tcgccccgcc 2220
cccagcgggc actcaggccg taccactgtg ccttcatggg ggtggagata gatcgtgggc 2280
tagtcctgcc gaggagagag gggttcttcc tcaaaaaata tgattatgta tagtattcgc 2340
atgattctag ttaacttgtt tcccttctgc ctgctcggac cctctacctg ccctacgaag 2400
ggggcggagt gcgttcctgc ctccccctgc tcttccgcgt ttggtgcgcg cctgcgcggt 2460
gcgtaggcgg cggagcgtac ttaagcttcg acgcaggagg cggggctgct cagtcctcca 2520
ggcgtcggta ctcagcggtg ttggaacttc gttgcttgct tgcctgtgcg cgcgtgcgcg 2580
gacatggcct caaacggtag gtaagggcgc gaggcgacgg cggcggcgca cccggccgag 2640
gcctcccagc tgggcttttc gttttcagtg ggaccggggc ggcgatcccg tgtgggattt 2700
tttggcgccc ctgtggcggg aagccgcgga gaagagtaac tggaggaggc tggtgtcgcc 2760
attttgtttc gctcctctgg ccctcgcgcg cggggcggga agtcttttct ttgcagtccg 2820
tttgcttggg gtgggcgttg ggagggacgc ttcttagggg tttgaagcgt caggtgaggg 2880
tggaaaacgc ccattctccg tggcctcgcc tcccccaact cccggccccg cgctcgagcc 2940
cgctttgtcg cagtgctgca tccgggcact cgcggcgcgc acgcgctctg cgggcccctc 3000
ccccttcgcg gcgcgggtac cccttccccg cctcgtgttg gttcagcttt ctgtcgcgag 3060
acccttcgcg gaagactcgg cggcgcgcgt ccggtgcccg gctaattttt tgtattttta 3120
ttagagatgg ggcttcacca tgttggtcag gccagtctcg aattcctgac ctcaagtgat 3180

```
ccacccacct cggcctccca aactgctggg attacaggca tgatccaccg tgcctggcct   3240
acgtggtcct ttttattcat cagtgcttga gttaaggaat ttagctttaa ttcaactctt   3300
tcagagtggc agctgaagat aatgtgattg tatttttctt ttgcagatta tacccaacaa   3360
gcaacccaaa ggtgagtgct atttttgggc ttccagagtt tgtagagggc aagggtggtc   3420
acgccatgtt ttctgatcac gctggttttc cttttattta gctatggggc ctaccccacc   3480
cagcccgggc agggctattc ccagcagagc agtcagccct acggacagca gagttacagt   3540
ggttatagcc agtccacgga cacttcaggc tatggccaga gcagctattc ttcttatggc   3600
cagagccaga acagtgagtc tttctcagcg ggtcacctct tcctactctt tctgaatatt   3660
gcttttcttt ttcttgtttt ttggagacgg agtctggtcc tgttgcccag gctggagtgc   3720
agtggtgctg tctcagctca ctgcaacatc agcctaccgg gttcaaacga ttctcctgcc   3780
tcagcctcct gagtagctgg gattacaggt acctgctacc acgcctggct aattttgtgt   3840
ttttagtaga gatggggttt cacgggtggt gctggagatg gtgttgggat tggcggggtg   3900
aaattggaac tgtactaaag agttggtaga agttgaagca ttaaatttag gctttgaaag   3960
gagggtaact atctttgcct atgagttgca acatcactaa cagcttctga gaggctggct   4020
ttatgagtat aggtattatg ttttctttaa cccattcctt acattttctc tttcctggtg   4080
gcttttgtga ctcccttttt cttatcctgg tagcaggcta tggaactcag tcaactcccc   4140
agggatatgg ctcgactggc ggctatggca gtagccagag ctcccaatcg tcttacgggc   4200
agcagtcctc ctaccctggc tatggccagc agccagctcc cagcagcacc tcgggaaggt   4260
acggtggtgt tgatgtcggg gaaggcttga aaagaggggt gaattgatga ggaatgataa   4320
agggaccagc agtaggagca gttcagaggt gtaattgggg taggggagcc tgtgttgggt   4380
acagagaatg gactccacta aaagtgaaag gaaattgggg gctatgctgg gattgtgatt   4440
gtgtttttttg tttgtttcc ctagttacgg tagcagttct cagagcagca gctatgggca   4500
gccccagagt gggagctaca gccagcagcc tagctatggt ggacagcagc aaagctatgg   4560
acagcagcaa agctataatc cccctcaggg ctatggacag cagaaccagt acaacagcag   4620
cagtggtggt ggaggtggag gtggaggtgg aggtgagatg tcttcagctt tgtctgcagc   4680
ccattttctt tttctttttt tttttttttt tgagacggag tcttgctctg tctctgttgc   4740
tgaggctgga gtgcagtggc acaatctcgg ctcactgcaa gctccgcctt ccgggttcgc   4800
gccagtctcc tgcctcagcc tcccgagtag ctgggactac aggcatccgc caccacgccc   4860
ggctaatttt ttgtattttt agtagagacg gggtttcacc atcgccttgg cctcccaaag   4920
tgctgggatt acaggcgtga gccactgtgc ctggtgtctg cagcccattt tctataagga   4980
tttgtattct cctgttttag cttaaaagag ggttcctgtc ttgtttccta gctgtctttt   5040
tactttcttt tgtccttcat tgcctggcac ttgtcaaacc ttttcaaacc ttttagtgct   5100
actttacaat ctttttgttt ttttttttta atcattcttt cttttctcac aggtaactat   5160
ggccaagatc aatcctccat gagtagtggt ggtggcagtg gtggcggtta tggcaatcaa   5220
gaccagagtg gtggaggtgg cagcggtggc tatggacagc aggaccgtgg aggccgcggc   5280
aggggtggca gtggtggcgg cggcggcggc ggcggtggtg gttacaaccg cagcagtggt   5340
ggctatgaac ccagaggtcg tggaggtggc cgtggaggca gaggtggcat ggggtaggtg   5400
tctcatgagc cagggagtat ctttggtggg gagtgtggag gattgcatga atctccctga   5460
agccagtccc tagtgcatgg tttagtattc ttgttgtcta gggatctgtg agggctttga   5520
```

```
tttgggggca gtgactttct ttttacatcc ccattttatt tttgtgagaa cttgggagcc   5580
tgaactccca tccataccac tgaatagaga ttttgagtaa tgatacttgt ttccaaaaaa   5640
aaacagagga aatagataac gtaacctttt aaagcaaaat ctttataaac tgtgtctgag   5700
aaattgcaca cgtgtgtgtg acatgctcaa aggtcagaca aggggtggtc aggaagggat   5760
gtattttagt agccacttgt atctttttcc aaaaacacct acccatgttt ggggaatgtt   5820
aaacaaaatc aaaaaacaac cttttgtagc cgttggaagc ttcatgtcct ttcttctaac   5880
ttgtcttctc cagcggaagt gaccgtggtg gcttcaataa atttggtggt aagtgaacag   5940
agtttccaaa attcccaact cccagcaatg ctttgtctga ttgttcattt gcagatgtct   6000
tagcgtgtta atttaaatgt caaaggtttt gaggtgtcca gaaccacctc cagaaagggg   6060
tagggtagaa tgccacctgt tgcctggtgt gtgctaacct ggagcaggta ggggtaagac   6120
tcaatagtca tcttttacca aatgggtttg ccccaggtta ataagagggg tctagtagtt   6180
tgctgaagtg tggagttgtc tctgtggaga ctcaagttac agatcttaag ggcctgcct    6240
agaattttct cctctgggca ggcgacccag gaaagggttt ggagtgaggc tgtgagcact   6300
tacttgatat tttacaagtt tggatttggt gttaattttt ttccttgtcc gtttttttcct  6360
gttgactaac ggctcatctt ttccttgttt ttgttttttt tttgttcttt ttttccatgt   6420
cactaaaggc cctcgggacc aaggatcacg tcatgactcc ggtgagttca cacgtggtgg   6480
catgaaaaga gtggctaaag tggtatcaag actgcctgga tgttctttga aactattata   6540
aaaaggaaac tgaaaaaaat ggggatagag aaggaaggga gttaggtgtg tccttagtta   6600
gcagtgagaa gtatttgtta cgaagtattt ctcagaaata cctggcttgt gggttccacc   6660
cccagtgatt taggtctgag aggaccctga aaatctacct ttctaacaag tactcctgag   6720
ccctggtttc catactgtat actgggtgtt aacatgtttc aaaggataat tgtcaaactg   6780
aatctgaaat ttatcagcat ggctggcata tagggactca aaagggatgt ggatttcttt   6840
ttagttgtct tccataaacc aaatgatacc agttgcttga tggatactag gtgctttagg   6900
ttttttcctg tgttttttat tttacctttt cacatttgca ttttctctgt tcaacaagca   6960
gaacaggata attcagacaa caacaccatc tttgtgcaag gcctgggtga gaatgttaca   7020
attgagtctg tggctgatta cttcaagcag attggtatta ttaaggtact tgtggagagg   7080
agtgggagct ttctgtcagt gttgtaggct tgtggatttc acacattagt aaaagcaagt   7140
ctttaatggt tgccagcagt aaaaacaagt cttagtggtt gttgccagct taatttgttg   7200
aggaaagagc cttagttact gttttctaaa agagaagttc tatcttaaca caaaaagtat   7260
aacttatcag agtaccctaa actcttgaga tttgtactct atagtaactt ttagttttat   7320
ctttcaatat tggagtgaga gacagttttc tttaatggag gtttacatgt gaggtaggaa   7380
gaagtaactg ggaagagggg agctgaagtt tgggaattat aaacctcatg ttctagagga   7440
agaagatgga aagggagtac tgtagccttt aaaattgatg ttacctcatt ttgctttctt   7500
cagacaaaca agaaaacggg acagcccatg attaatttgt acacagacag ggaaactggc   7560
aagctgaagg gagaggcaac ggtctctttt gatgacccac cttcagctaa agcagctatt   7620
gactggtttg atggtatgta tgagaaggct ggcagaggtg gggctgggga tatagggcag   7680
caagccttag gaaacaagcc atagtttgag ggttcttttg agtcttccaa cacttacttt   7740
agctgcggtt tcaggtagtc tcatttttgc ttatgtgtca gcagattata aaccatttga   7800
gaaaggcacg cttctcttgt attttcggat taatgtgtct tgcatttaaa gtctgttgat   7860
gattttttgt ttctctaggt aaagaattct ccggaaatcc tatcaaggtc tcatttgcta   7920
```

```
ctcgccgggc agactttaat cggggtggtg gcaatggtcg tggaggccga gggcgaggag   7980
gtgaggagct acctgctagt ggtgcagagg ggtaatgggg agagtgcaga agatggtaaa   8040
ggcttgcatg gaatgggtta gatttaccaa acttggagag ggagcagacc catacttggt   8100
ctatctgcat taggacccat gggccgtgga ggctatggag gtggtggcag tggtggtggt   8160
ggccgaggag gatttcccag tggaggtggt ggcggtggag gacagcagcg agctggtgac   8220
tggaagtgtc ctaatccgtg agtgaaactt aatttttttc ttagttctct tgcatgcgtg   8280
ctctttgata tattggtact gaggtatgtg cgtgttttcc aaagaagtaa atgtcaaggc   8340
cacactgttg gggtcagatt tagccaaaag cttacctagg taaggttgat gtaatgggaa   8400
aggtaatgga ttgggttcag taatactgat ttttgttcct gactctgaga agcaagccgt   8460
tttgtctttc tgaagcttca gtttcctcac tgtatctcta aagtcaccgt agtttcttcc   8520
tagttctagg tcttgcctat tccccatcgc tccagactga ttgtcttcct ttctccttag   8580
cacctgtgag aatatgaact tctcttggag gaatgaatgc aaccagtgta aggcccctaa   8640
accagatggc ccaggagggg gaccaggtgg ctctcacatg ggtaagaaag gcagacctgg   8700
tgctagggag ctgggaccaa agaatcctta atttttcagc ggggaggctc ggggaacata   8760
ggggaatggg aatatgatag atcttgtttc ttttgtccta gggggtaact acggggatga   8820
tcgtcgtggt ggcagaggag gctatgatcg aggcggctac cggggccgcg gcggggaccg   8880
tggaggcttc cgaggggggcc ggggtggtgg ggacagaggt ggctttggcc ctggcaagat   8940
ggattccagg taagacttta aatcagaata aaaaagtaga gcagttgaac agaggccata   9000
ggataacagg gttttgttga gaaagtggtt tcattttgag ggctaggtgg aaagacctga   9060
ggttgtaacc agtagtggag agggaaggaa aattaactca gggggagtga atctgtagac   9120
ccacttgaga taagatactc gctgggttag gtaggagggg cagataggat atctaggctt   9180
ggagaggctg gtaactcaaa tataatggat acttaatttt tttttttttt tttgcagggg   9240
tgagcacaga caggatcgca gggagaggcc gtattaatta gcctggctcc ccaggttctg   9300
gaacagcttt ttgtcctgta cccagtgtta ccctcgttat tttgtaacct tccaattcct   9360
gatcacccaa gggttttttt gtgtcggact atgtaattgt aactatacct ctggttccca   9420
ttaaaagtga ccattttagt taaattttgt tcctcttccc ccttttcact ttcctggaag   9480
atcgatgtcc cgatcaggaa ggtagagagt tttcctgttc agattaccct gcccagcagg   9540
aactggaata cagtgttcgg ggagaaggcc aaatgatatc cttgagagca gagattaaac   9600
ttttctgtca tggggaaagt tggtgtataa atgagaaatg aagaacatgg gatgtcatga   9660
gtgttggcct aaatttgccc agctatgggg aatttttcct ttaccacatt tatttgcata   9720
ctggtcttag tttatttgca gcagtttatc ccttttttaag aactctttga tcttttggcc   9780
cttttaatgg tgaggctcaa acaaactaca tttaaatggg gcagtattca gatttgacca   9840
tggtggagag cgcttagcca ctctgggtct ttcacaggaa ggagagtaac tgagtgctgc   9900
aggagtttgt ggagtggagt caggatctag gaggtgagtg actcccttcc tagctgccct   9960
ggtgaacagc gcttgggtag atacctgcta taaggagact ggtctggctg ggttactttc  10020
acatcctgcc tgtactcaga gggcttgagg tcattgacat tatgagattt taggcttgat  10080
cccttttga ttggagggtg gaaggccctc ctaag                             10115
```

<210> SEQ ID NO 2
<211> LENGTH: 2002
<212> TYPE: DNA

<213> ORGANISM: Homo sapiens

<400> SEQUENCE: 2

```
cggggctgct cagtcctcca ggcgtcggta ctcagcggtg ttggaacttc gttgcttgct     60
tgcctgtgcg cgcgtgcgcg gacatggcct caaacgatta tacccaacaa gcaacccaaa    120
gctatggggc ctaccccacc cagcccgggc agggctattc ccagcagagc agtcagccct    180
acggacagca gagttacagt ggttatagcc agtccacgga cacttcaggc tatggccaga    240
gcagctattc ttcttatggc cagagccaga acacaggcta tggaactcag tcaactcccc    300
agggatatgg ctcgactggc ggctatggca gtagccagag ctcccaatcg tcttacgggc    360
agcagtcctc ctaccctggc tatggccagc agccagctcc cagcagcacc tcgggaagtt    420
acggtagcag ttctcagagc agcagctatg ggcagcccca gagtgggagc tacagccagc    480
agcctagcta tggtggacag cagcaaagct atggacagca gcaaagctat aatcccccctc    540
agggctatgg acagcagaac cagtacaaca gcagcagtgg tggtggaggt ggaggtggag    600
gtggaggtaa ctatggccaa gatcaatcct ccatgagtag tggtggtggc agtggtggcg    660
gttatggcaa tcaagaccag agtggtggag gtggcagcgg tggctatgga cagcaggacc    720
gtggaggccg cggcaggggt ggcagtggtg gcggcggcgg cggcggcggt ggtggttaca    780
accgcagcag tggtggctat gaacccagag gtcgtggagg tggccgtgga ggcagaggtg    840
gcatgggcgg aagtgaccgt ggtggcttca ataaatttgg tggccctcgg gaccaaggat    900
cacgtcatga ctccgaacag gataattcag acaacaacac catctttgtg caaggcctgg    960
gtgagaatgt tacaattgag tctgtggctg attacttcaa gcagattggt attattaaga   1020
caaacaagaa aacgggacag cccatgatta atttgtacac agacagggaa actggcaagc   1080
tgaagggaga ggcaacggtc tcttttgatg acccaccttc agctaaagca gctattgact   1140
ggtttgatgg taaagaattc tccggaaatc ctatcaaggt ctcatttgct actcgccggg   1200
cagactttaa tcggggtggt ggcaatggtc gtggaggccg agggcgagga ggacccatgg   1260
gccgtggagg ctatggaggt ggtggcagtg gtggtggtgg ccgaggagga tttcccagtg   1320
gaggtggtgg cggtggagga cagcagcgag ctggtgactg gaagtgtcct aatcccacct   1380
gtgagaatat gaacttctct tggaggaatg aatgcaacca gtgtaaggcc cctaaaccag   1440
atggcccagg agggggacca ggtggctctc acatgggggg taactacggg gatgatcgtc   1500
gtggtggcag aggaggctat gatcgaggcg gctaccgggg ccgcggcggg gaccgtggag   1560
gcttccgagg gggccggggt ggtggggaca gaggtggctt tggccctggc aagatggatt   1620
ccaggggtga gcacagacag gatcgcaggg agaggccgta ttaattagcc tggctcccca   1680
ggttctggaa cagctttttg tcctgtaccc agtgttaccc tcgttatttt gtaaccttcc   1740
aattcctgat cacccaaggg tttttttgtg tcggactatg taattgtaac tatacctctg   1800
gttcccatta aaagtgacca ttttagttaa attttgttcc tcttcccccct tttcactttc   1860
ctggaagatc gatgtcccga tcaggaaggt agagagtttt cctgttcaga ttaccctgcc   1920
cagcaggaac tggaatacag tgttcgggga gaaggccaaa tgatatcctt gagagcagag   1980
attaaacttt tctgtcatgg gg                                             2002
```

<210> SEQ ID NO 3
<211> LENGTH: 1581
<212> TYPE: DNA
<213> ORGANISM: Homo sapiens

<400> SEQUENCE: 3

```
atggcctcaa acgattatac ccaacaagca acccaaagct atggggccta ccccacccag     60

cccgggcagg gctattccca gcagagcagt cagccctacg gacagcagag ttacagtggt    120

tatagccagt ccacggacac ttcaggctat ggccagagca gctattcttc ttatggccag    180

agccagaaca caggctatgg aactcagtca actccccagg gatatggctc gactggcggc    240

tatggcagta gccagagctc ccaatcgtct tacgggcagc agtcctccta ccctggctat    300

ggccagcagc cagctcccag cagcacctcg ggaagttacg gtagcagttc tcagagcagc    360

agctatgggc agccccagag tgggagctac agccagcagc ctagctatgg tggacagcag    420

caaagctatg gacagcagca aagctataat ccccctcagg gctatggaca gcagaaccag    480

tacaacagca gcagtggtgg tggaggtgga ggtggaggtg gaggtaacta tggccaagat    540

caatcctcca tgagtagtgg tggtggcagt ggtggcggtt atggcaatca agaccagagt    600

ggtggaggtg gcagcggtgg ctatggacag caggaccgtg gaggccgcgg caggggtggc    660

agtggtggcg gcggcggcgg cggcggtggt ggttacaacc gcagcagtgg tggctatgaa    720

cccagaggtc gtggaggtgg ccgtggaggc agaggtggca tgggcggaag tgaccgtggt    780

ggcttcaata aatttggtgg ccctcgggac caaggatcac gtcatgactc cgaacaggat    840

aattcagaca acaacaccat ctttgtgcaa ggcctgggtg agaatgttac aattgagtct    900

gtggctgatt acttcaagca gattggtatt attaagacaa acaagaaaac gggacagccc    960

atgattaatt tgtacacaga cagggaaact ggcaagctga agggagaggc aacggtctct   1020

tttgatgacc caccttcagc taaagcagct attgactggt ttgatggtaa agaattctcc   1080

ggaaatccta tcaaggtctc atttgctact cgccgggcag actttaatcg gggtggtggc   1140

aatggtcgtg gaggccgagg gcgaggagga cccatgggcc gtggaggcta tggaggtggt   1200

ggcagtggtg gtggtggccg aggaggattt cccagtggag gtggtggcgg tggaggacag   1260

cagcgagctg gtgactggaa gtgtcctaat cccacctgtg agaatatgaa cttctcttgg   1320

aggaatgaat gcaaccagtg taaggcccct aaaccagatg gcccaggagg gggaccaggt   1380

ggctctcaca tgggggggtaa ctacggggat gatcgtcgtg gtggcagagg aggctatgat   1440

cgaggcggct accggggccg cggcggggac cgtggaggct tccgaggggg ccggggtggt   1500

ggggacagag gtggctttgg ccctggcaag atggattcca ggggtgagca cagacaggat   1560

cgcagggaga ggccgtatta a                                             1581
```

<210> SEQ ID NO 4
<211> LENGTH: 526
<212> TYPE: PRT
<213> ORGANISM: Homo sapiens

<400> SEQUENCE: 4

```
Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
```

```
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Ser Gly Gly Gly Gly Gly Gly Gly Gly Gly Gly Asn
                165                 170                 175

Tyr Gly Gln Asp Gln Ser Ser Met Ser Ser Gly Gly Gly Ser Gly Gly
            180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Gly Tyr Asn Arg Ser Ser Gly Gly Tyr Glu
225                 230                 235                 240

Pro Arg Gly Arg Gly Gly Gly Arg Gly Gly Arg Gly Gly Met Gly Gly
                245                 250                 255

Ser Asp Arg Gly Gly Phe Asn Lys Phe Gly Gly Pro Arg Asp Gln Gly
            260                 265                 270

Ser Arg His Asp Ser Glu Gln Asp Asn Ser Asp Asn Asn Thr Ile Phe
        275                 280                 285

Val Gln Gly Leu Gly Glu Asn Val Thr Ile Glu Ser Val Ala Asp Tyr
    290                 295                 300

Phe Lys Gln Ile Gly Ile Ile Lys Thr Asn Lys Lys Thr Gly Gln Pro
305                 310                 315                 320

Met Ile Asn Leu Tyr Thr Asp Arg Glu Thr Gly Lys Leu Lys Gly Glu
                325                 330                 335

Ala Thr Val Ser Phe Asp Asp Pro Pro Ser Ala Lys Ala Ala Ile Asp
            340                 345                 350

Trp Phe Asp Gly Lys Glu Phe Ser Gly Asn Pro Ile Lys Val Ser Phe
        355                 360                 365

Ala Thr Arg Arg Ala Asp Phe Asn Arg Gly Gly Gly Asn Gly Arg Gly
    370                 375                 380

Gly Arg Gly Arg Gly Gly Pro Met Gly Arg Gly Gly Tyr Gly Gly Gly
385                 390                 395                 400

Gly Ser Gly Gly Gly Gly Arg Gly Gly Phe Pro Ser Gly Gly Gly Gly
                405                 410                 415

Gly Gly Gly Gln Gln Arg Ala Gly Asp Trp Lys Cys Pro Asn Pro Thr
            420                 425                 430

Cys Glu Asn Met Asn Phe Ser Trp Arg Asn Glu Cys Asn Gln Cys Lys
        435                 440                 445

Ala Pro Lys Pro Asp Gly Pro Gly Gly Gly Pro Gly Gly Ser His Met
    450                 455                 460

Gly Gly Asn Tyr Gly Asp Asp Arg Arg Gly Gly Arg Gly Gly Tyr Asp
465                 470                 475                 480

Arg Gly Gly Tyr Arg Gly Arg Gly Gly Asp Arg Gly Gly Phe Arg Gly
                485                 490                 495

Gly Arg Gly Gly Gly Asp Arg Gly Gly Phe Gly Pro Gly Lys Met Asp
            500                 505                 510
```

```
Ser Arg Gly Glu His Arg Gln Asp Arg Arg Glu Arg Pro Tyr
        515                 520                 525


<210> SEQ ID NO 5
<211> LENGTH: 48
<212> TYPE: PRT
<213> ORGANISM: Homo sapiens

<400> SEQUENCE: 5

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 6
<211> LENGTH: 48
<212> TYPE: PRT
<213> ORGANISM: Pan troglodytes

<400> SEQUENCE: 6

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 7
<211> LENGTH: 47
<212> TYPE: PRT
<213> ORGANISM: Macaca mulatta

<400> SEQUENCE: 7

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro
        35                  40                  45


<210> SEQ ID NO 8
<211> LENGTH: 35
<212> TYPE: PRT
<213> ORGANISM: Sciurus carolinensis

<400> SEQUENCE: 8

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser
        35


<210> SEQ ID NO 9
<211> LENGTH: 47
<212> TYPE: PRT
<213> ORGANISM: Loxodonta africana

<400> SEQUENCE: 9
```

```
Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro
        35                  40                  45


<210> SEQ ID NO 10
<211> LENGTH: 48
<212> TYPE: PRT
<213> ORGANISM: Bos taurus

<400> SEQUENCE: 10

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 11
<211> LENGTH: 48
<212> TYPE: PRT
<213> ORGANISM: Mus musculus

<400> SEQUENCE: 11

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 12
<211> LENGTH: 48
<212> TYPE: PRT
<213> ORGANISM: Rattus norvegicus

<400> SEQUENCE: 12

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 13
<211> LENGTH: 48
<212> TYPE: PRT
<213> ORGANISM: Erinaceus europaeus

<400> SEQUENCE: 13

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45
```

<210> SEQ ID NO 14
<211> LENGTH: 47
<212> TYPE: PRT
<213> ORGANISM: Procavia capensis

<400> SEQUENCE: 14

Tyr Asp Arg Gly Gly Tyr Arg Gly Arg Gly Gly Asp Arg Gly Gly Phe
1 5 10 15

Arg Gly Gly Arg Gly Gly Gly Asp Arg Gly Gly Phe Gly Pro Gly Lys
20 25 30

Met Asp Ser Arg Gly Glu His Arg Gln Asp Arg Arg Glu Arg Pro
35 40 45

<210> SEQ ID NO 15
<211> LENGTH: 47
<212> TYPE: PRT
<213> ORGANISM: Erinaceus concolor

<400> SEQUENCE: 15

Tyr Asp Gly Gly Tyr Arg Gly Arg Gly Gly Asp Arg Gly Gly Phe Gln
1 5 10 15

Gly Gly Trp Gly Gly Gly Asp Arg Gly Gly Phe Gly Pro Gly Lys Met
20 25 30

Asp Ser Arg Gly Asp His Arg Gln Asp His Arg Glu Arg Pro Tyr
35 40 45

<210> SEQ ID NO 16
<211> LENGTH: 46
<212> TYPE: PRT
<213> ORGANISM: Myotis lucifugus

<400> SEQUENCE: 16

Tyr Asp Gln Gly Gly Tyr Gly Gly His Asp Gly Asp Arg Gly Gly Phe
1 5 10 15

Arg Gly Arg Gly Ala Gly Asp Arg Gly Gly Phe Val Pro Gly Lys Met
20 25 30

Asp Ser Gly Asp His Arg Gln Asp Arg Arg Glu Arg Pro Tyr
35 40 45

<210> SEQ ID NO 17
<211> LENGTH: 42
<212> TYPE: PRT
<213> ORGANISM: Dasypus novemcinctus

<400> SEQUENCE: 17

Cys Asp Trp Gly Ser Tyr Gly Gly Arg Asp Cys Gly Phe Gly Gly Asp
1 5 10 15

Gly Gly Asp Arg Gly Gly Ser Gly His Gly Lys Val Asp Ser Arg Gly
20 25 30

Gly His Arg Gln Asp Arg Trp Glu Arg Pro
35 40

<210> SEQ ID NO 18
<211> LENGTH: 48
<212> TYPE: PRT
<213> ORGANISM: Didelphis marsupialis

<400> SEQUENCE: 18

Tyr Asp Arg Gly Gly Tyr Arg Gly Arg Gly Gly Asp Arg Gly Gly Phe
1 5 10 15

Arg Gly Gly Arg Gly Gly Gly Asp Arg Gly Gly Phe Gly Pro Gly Lys

```
            20                  25                  30

Met Asp Ser Arg Gly Glu His Arg Gln Asp Arg Arg Glu Arg Pro Tyr
        35                  40                  45


<210> SEQ ID NO 19
<211> LENGTH: 48
<212> TYPE: PRT
<213> ORGANISM: Canis familiaris

<400> SEQUENCE: 19

Tyr Asp Arg Gly Gly Tyr Arg Gly Arg Gly Gly Asp Arg Gly Gly Phe
1               5                   10                  15

Arg Gly Gly Arg Gly Gly Gly Asp Arg Gly Gly Phe Gly Pro Gly Lys
            20                  25                  30

Met Asp Ser Arg Gly Glu His Arg Gln Asp Arg Arg Glu Arg Pro Tyr
        35                  40                  45


<210> SEQ ID NO 20
<211> LENGTH: 47
<212> TYPE: PRT
<213> ORGANISM: Xenopus laevis

<400> SEQUENCE: 20

Phe Asp Arg Gly Gly Phe Arg Gly Arg Gly Gly Asp Arg Gly Gly Phe
1               5                   10                  15

Arg Gly Gly Arg Gly Gly Asp Arg Gly Gly Phe Gly Pro Gly Lys Met
            20                  25                  30

Asp Ser Arg Gly Asp His Arg Gln Asp Arg Arg Asp Arg Pro Tyr
        35                  40                  45


<210> SEQ ID NO 21
<211> LENGTH: 47
<212> TYPE: PRT
<213> ORGANISM: Danio rerio

<400> SEQUENCE: 21

Phe Asp Arg Gly Gly Phe Arg Gly Arg Gly Gly Asp Arg Gly Gly Phe
1               5                   10                  15

Arg Gly Gly Arg Gly Gly Asp Arg Gly Gly Phe Gly Pro Gly Lys Met
            20                  25                  30

Asp Ser Arg Gly Asp His Arg His Asp Arg Arg Asp Arg Pro Tyr
        35                  40                  45


<210> SEQ ID NO 22
<211> LENGTH: 47
<212> TYPE: PRT
<213> ORGANISM: Tetraodon nigroviridis

<400> SEQUENCE: 22

Phe Asp Arg Gly Gly Phe Arg Gly Arg Gly Gly Asp Arg Gly Gly Phe
1               5                   10                  15

Arg Gly Gly Arg Gly Gly Glu Arg Gly Gly Tyr Gly Pro Gly Lys Met
            20                  25                  30

Asp Ala Arg Gly Asp Arg Arg Gln Glu Arg Arg Gly Arg Pro Tyr
        35                  40                  45
```